(12) United States Patent
Nakagaki

(10) Patent No.: US 11,249,045 B2
(45) Date of Patent: Feb. 15, 2022

(54) GAS SENSOR, AND METHOD FOR MEASURING CONCENTRATIONS OF PLURALITY OF TARGET COMPONENTS IN GAS TO BE MEASURED

(71) Applicant: NGK INSULATORS, LTD., Nagoya (JP)

(72) Inventor: Kunihiko Nakagaki, Kronberg im Taunus (DE)

(73) Assignee: NGK INSULATORS, LTD., Nagoya (JP)

( * ) Notice: Subject to any disclaimer, the term of this patent is extended or adjusted under 35 U.S.C. 154(b) by 114 days.

(21) Appl. No.: 16/226,687

(22) Filed: Dec. 20, 2018

(65) Prior Publication Data

US 2019/0128833 A1    May 2, 2019

Related U.S. Application Data

(63) Continuation of application No. PCT/JP2017/022946, filed on Jun. 22, 2017.

(30) Foreign Application Priority Data

Jun. 23, 2016 (JP) .............................. JP2016-124414

(51) Int. Cl.
*G01N 27/409* (2006.01)
*G01N 27/419* (2006.01)
(Continued)

(52) U.S. Cl.
CPC ........... *G01N 27/409* (2013.01); *F01N 3/208* (2013.01); *F01N 11/007* (2013.01); *G01N 27/41* (2013.01);
(Continued)

(58) Field of Classification Search
CPC ............. G01N 27/4167; G01N 27/417; G01N 27/419; G01N 27/4175; G01N 27/407;
(Continued)

(56) References Cited

U.S. PATENT DOCUMENTS 7,690,799 B2   4/2010   Nestorovic et al.
8,382,973 B2   2/2013   Sugaya et al.
(Continued)

FOREIGN PATENT DOCUMENTS

DE   10 2008 006 633 A1   7/2009
EP        0 930 501 A2    7/1999
(Continued)

OTHER PUBLICATIONS

Extended European Search Report received in corresponding European Application No. 17815469.6 dated Oct. 11, 2019.
(Continued)

*Primary Examiner* — Mayla Gonzalez Ramos
(74) *Attorney, Agent, or Firm* — Mattingly & Malur, PC

(57) ABSTRACT

A gas sensor, and a method for measuring the concentrations of a plurality of target components in a gas to be measured are disclosed. The gas sensor is provided with: a specific component measurement means which measures the concentration of a specific component in a measurement chamber; a preliminary oxygen concentration control means which controls the oxygen concentration in a preliminary adjustment chamber; a drive control means which controls the driving and stopping of the preliminary oxygen concentration control means; and a target component acquisition means which, on the basis of the difference between sensor outputs from the specific component measurement means when the preliminary oxygen concentration control means is being driven and when the preliminary oxygen concentration control means is stopped, and one of the respective
(Continued)

sensor outputs, acquires the concentrations of a first target component and a second target component.

22 Claims, 20 Drawing Sheets

(51) Int. Cl.
    *G01N 33/00*     (2006.01)
    *F01N 3/20*     (2006.01)
    *F01N 11/00*     (2006.01)
    *G01N 27/41*     (2006.01)

(52) U.S. Cl.
    CPC ....... *G01N 27/419* (2013.01); *G01N 33/0037* (2013.01); *G01N 33/0054* (2013.01); *F01N 2560/021* (2013.01); *F01N 2560/026* (2013.01); *F01N 2610/02* (2013.01); *F01N 2610/144* (2013.01)

(58) Field of Classification Search
    CPC ... G01N 27/4074; G01N 27/409; G01N 27/41
    See application file for complete search history.

(56) References Cited

U.S. PATENT DOCUMENTS

| | | |
|---|---|---|
| 9,291,819 B2 | 3/2016 | Ferri |
| 9,939,638 B2 | 4/2018 | Yagi et al. |
| 2005/0211554 A1* | 9/2005 | Kurachi ............. G01N 27/4071 204/426 |
| 2007/0080074 A1 | 4/2007 | Wang et al. |
| 2008/0011051 A1 | 1/2008 | Lemire |
| 2009/0120791 A1 | 5/2009 | Miyashita et al. |
| 2011/0048970 A1* | 3/2011 | Sugaya ................ G01N 27/419 205/781 |
| 2015/0061976 A1 | 3/2015 | Ferri |
| 2015/0276659 A1 | 10/2015 | Sekiya et al. |
| 2019/0128166 A1 | 5/2019 | Nakagaki |

FOREIGN PATENT DOCUMENTS

| | | |
|---|---|---|
| JP | 2009-511859 A | 3/2009 |
| JP | 2009-243942 A | 10/2009 |
| JP | 2012-501472 A | 1/2012 |
| JP | 2013-068632 A | 4/2013 |
| JP | 2015-87619 A | 5/2015 |
| JP | 2015-200643 A | 11/2015 |
| WO | 2015/141745 A1 | 9/2015 |
| WO | 2016/005520 A1 | 1/2016 |

OTHER PUBLICATIONS

International Search Report of PCT/JP2017/022946 dated Aug. 29, 2017.

Japanese Office Action received in corresponding Japanese Application No. 2017-545057 dated Oct. 23, 2019.

\* cited by examiner 10A (10B)

FIG. 6

| | NO CONCENTRATION (ppm) | NH₃ CONCENTRATION (ppm) | Ip3off (μA) | Ip3on (μA) | ΔIp3 (μA) | POINT |
|---|---|---|---|---|---|---|
| 100 ppm SYSTEM | 100 | 0.0 | 2.137 | 2.137 | 0.000 | p1 |
| | 80 | 17.6 | 2.137 | 2.103 | 0.034 | p2 |
| | 60 | 35.2 | 2.137 | 2.069 | 0.068 | p3 |
| | 40 | 52.8 | 2.137 | 2.035 | 0.102 | p4 |
| | 20 | 70.4 | 2.137 | 2.000 | 0.137 | p5 |
| | 0 | 88.0 | 2.137 | 1.966 | 0.171 | p6 |
| 50 ppm SYSTEM | 50 | 0.0 | 1.070 | 1.070 | 0.000 | p7 |
| | 40 | 8.8 | 1.070 | 1.053 | 0.017 | p8 |
| | 30 | 17.6 | 1.070 | 1.036 | 0.034 | p9 |
| | 20 | 26.4 | 1.070 | 1.019 | 0.051 | p10 |
| | 10 | 35.2 | 1.070 | 1.002 | 0.068 | p11 |
| | 0 | 44.0 | 1.070 | 0.985 | 0.085 | p12 |
| 25 ppm SYSTEM | 25 | 0.0 | 0.537 | 0.537 | 0.000 | p13 |
| | 20 | 4.4 | 0.537 | 0.528 | 0.009 | p14 |
| | 15 | 8.8 | 0.537 | 0.519 | 0.017 | p15 |
| | 10 | 13.2 | 0.537 | 0.511 | 0.026 | p16 |
| | 5 | 17.6 | 0.537 | 0.502 | 0.034 | p17 |
| | 0 | 22.0 | 0.537 | 0.494 | 0.043 | p18 |
| 0 ppm SYSTEM | 0 | 0.0 | 0.003 | 0.003 | 0.000 | p19 |
| | 0 | 20.0 | 0.488 | 0.449 | 0.039 | p20 |
| | 0 | 40.0 | 0.973 | 0.895 | 0.078 | p21 |
| | 0 | 60.0 | 1.458 | 1.342 | 0.116 | p22 |
| | 0 | 80.0 | 1.943 | 1.788 | 0.155 | p23 |
| | 0 | 100.0 | 2.428 | 2.234 | 0.194 | p24 |

| | NO CONCENTRATION (ppm) | NO₂ CONCENTRATION (ppm) | Ip3on (μA) | Ip3off (μA) | ΔIp3 (μA) | POINT |
|---|---|---|---|---|---|---|
| 500 ppm SYSTEM | 500 | 0.0 | 10.67 | 10.67 | 0.00 | p101 |
| | 400 | 116.0 | 10.91 | 10.67 | 0.23 | p102 |
| | 300 | 233.0 | 11.14 | 10.67 | 0.47 | p103 |
| | 200 | 349.0 | 11.37 | 10.67 | 0.70 | p104 |
| | 100 | 465.0 | 11.60 | 10.67 | 0.93 | p105 |
| | 0 | 582.0 | 11.84 | 10.67 | 1.16 | p106 |
| 250 ppm SYSTEM | 250 | 0.0 | 5.34 | 5.34 | 0.00 | p107 |
| | 200 | 58.0 | 5.45 | 5.34 | 0.12 | p108 |
| | 150 | 116.0 | 5.57 | 5.34 | 0.23 | p109 |
| | 100 | 175.0 | 5.69 | 5.34 | 0.35 | p110 |
| | 50 | 233.0 | 5.80 | 5.34 | 0.47 | p111 |
| | 0 | 291.0 | 5.92 | 5.34 | 0.58 | p112 |
| 100 ppm SYSTEM | 100 | 0.0 | 2.14 | 2.14 | 0.00 | p113 |
| | 80 | 23.3 | 2.18 | 2.14 | 0.05 | p114 |
| | 60 | 46.6 | 2.23 | 2.14 | 0.09 | p115 |
| | 40 | 69.8 | 2.28 | 2.14 | 0.14 | p116 |
| | 20 | 93.1 | 2.32 | 2.14 | 0.19 | p117 |
| | 0 | 116.4 | 2.37 | 2.14 | 0.23 | p118 |
| 0 ppm SYSTEM | 0 | 0.0 | 0.00 | 0.00 | 0.00 | — |

FIG. 18A

NO OUTPUT

Th1

EQUIVALENT POINT t0
EQUIVALENT POINT t1
EQUIVALENT POINT t2
EQUIVALENT POINT t3
EQUIVALENT POINT t4
EQUIVALENT POINT
EQUIVALENT POINT

FIG. 18B $NH_3$ OUTPUT

DEGREE OF OPENING OF UREA INJECTOR

OPENED

CLOSED

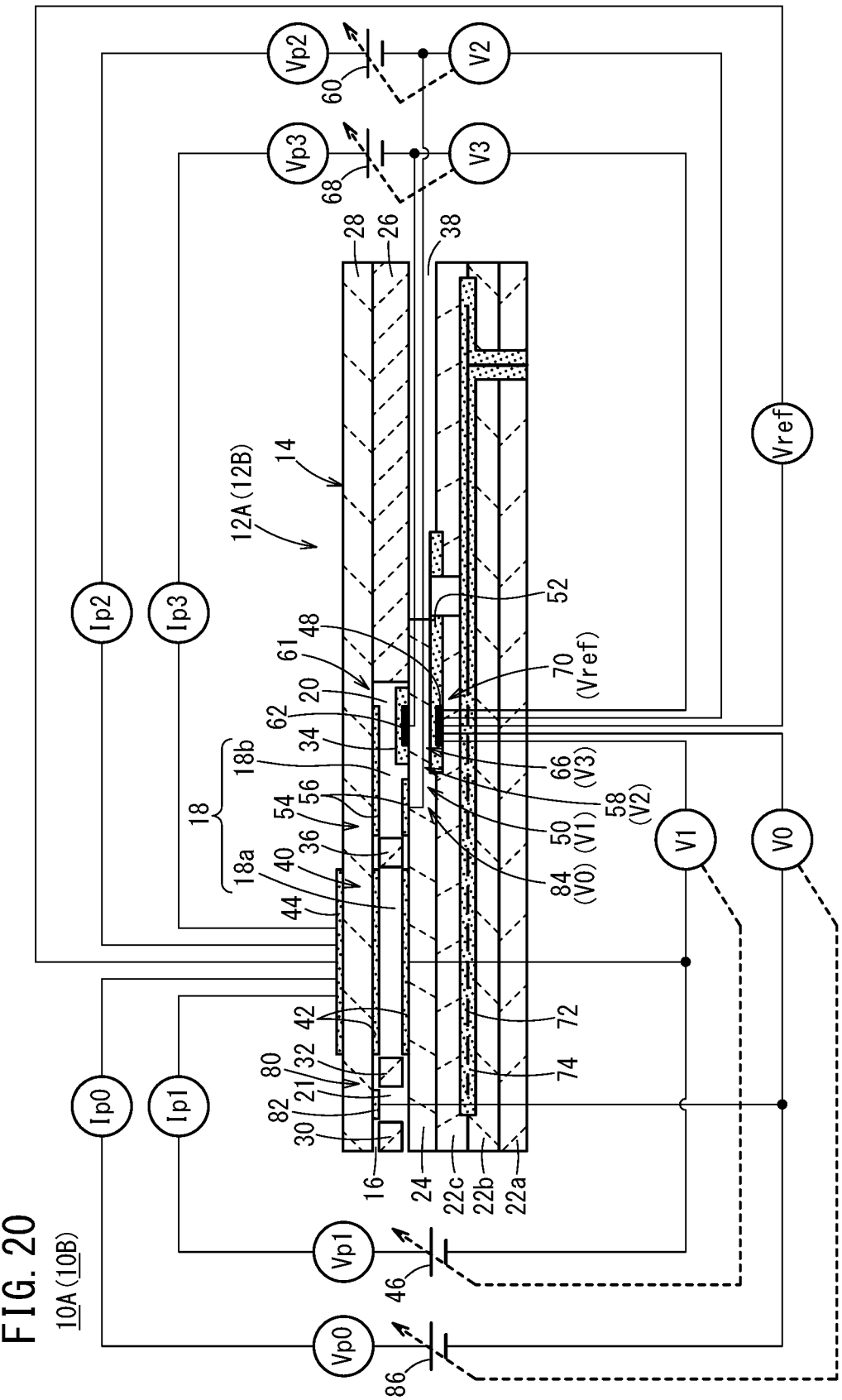

GAS SENSOR, AND METHOD FOR MEASURING CONCENTRATIONS OF PLURALITY OF TARGET COMPONENTS IN GAS TO BE MEASURED

CROSS-REFERENCE TO RELATED APPLICATIONS

This application is a Continuation of International Application No. PCT/JP2017/022946 filed on Jun. 22, 2017, which is based upon and claims the benefit of priority from Japanese Patent Application No. 2016-124414 filed on Jun. 23, 2016, the contents all of which are incorporated herein by reference.

TECHNICAL FIELD

The present invention relates to a gas sensor, which is capable of measuring respective concentrations of a plurality of target components in a gas to be measured, as well as to a method of measuring concentrations of a plurality of target components in a gas to be measured.

BACKGROUND ART

Conventionally, an NOx sensor (a serially arranged two-chamber type NOx sensor) having a serially arranged two-chamber structure, and a NOx measurement method using the same (for example, refer to Japanese Laid-Open Patent Publication No. 2015-200643), and a mixed potential type, or a variable resistance type $NO_2$ sensor in which an oxide semiconductor electrode is used, or an $NH_3$ sensor are known (for example, refer to Japanese Laid-Open Patent Publication No. 2013-068632 and Japanese Laid-Open Patent Publication No. 2009-243942).

Further, a method of measuring an $NH_3$ concentration using a mixed potential of an oxide semiconductor electrode is known. This method is a method in which the NOx concentration is measured by another sensor, and in the case that NO and $NO_2$ are not present, the mixed potential of the oxide semiconductor electrode is used as is, whereas, in the case that NO and $NO_2$ are present, a correction is added to the mixed potential of the oxide semiconductor electrode (see, for example, Japanese Laid-Open Patent Publication No. 2009-511859 (PCT)).

SUMMARY OF INVENTION

In recent years, there is a tendency for regulations in regard to $CO_2$ emission levels to be strengthened, and the adoption rate of diesel vehicles is increasing in respective countries. Diesel engines using lean combustion possess a disadvantage in that it is difficult to purify NOx in exhaust gas that contains an excessive amount of oxygen instead of a small amount of $CO_2$ emissions. For this reason, similar to strengthening regulations concerning $CO_2$ emissions, regulations concerning NOx emissions are also being strengthened. Currently, a selective reduction type catalyst system (hereinafter referred to as an SCR system) which can perform NOx purification without impairing $CO_2$ emission, that is, without a loss in fuel consumption, occupies the mainstream of NOx purification. In such an SCR system, injected urea is reacted with exhaust gas to produce ammonia, and the ammonia and NOx are reacted and are thereby decomposed into $N_2$ and $O_2$. In the SCR system, in order that the NOx purification efficiency is made close to 100%, it is necessary to increase the injected amount of urea. However, if the injected amount of urea is increased, unreacted ammonia may be discharged into the atmosphere. Therefore, a sensor capable of distinguishing between NOx and ammonia is required.

Furthermore, in the United States, preparations are being advanced with respect to obligations for individual failure diagnosis of oxidation catalysts (hereinafter referred to as DOC catalysts), diesel particulate filters (hereinafter referred to as DPF), and selective reduction type catalysts (hereinafter referred to as SCR catalysts). Although failure diagnosis of DPF and SCR catalysts are possible with existing PM sensors and NOx sensors, an effective failure diagnosis technique has not been discovered with respect to DOC catalysts. Currently, a method of measuring an amount of hydrocarbons (hereinafter referred to as HC) leaking downstream from a DOC catalyst at a low temperature of 200° C. or less, and a method of judging a failure from a ratio of NO and $NO_2$ that are discharged downstream from a DOC catalyst are recommended. In particular, in the ratio of NO and $NO_2$, since a reduction in $NO_2$ occurs earlier than an increase in the HC outflow amount, such a method is expected to be a safer method of fault diagnosis. For this purpose, a sensor that is capable of distinguishing between NO and $NO_2$ is demanded.

In the NOx sensor and the NOx measurement method described in the aforementioned Japanese Laid-Open Patent Publication No. 2015-200643, NO, $NO_2$, and $NH_3$ are converted into NO, and after conversion thereof, the NO is decomposed, and a generated amount or a concentration of $O_2$ is measured. Therefore, although the total amount of NO, $NO_2$, and $NH_3$ can be measured, it is not possible to distinguish between these respective components.

Although the oxide semiconductor electrodes described in Japanese Laid-Open Patent Publication No. 2013-068632 and Japanese Laid-Open Patent Publication 2009-243942 are excellent in terms of the selectivity of NO and $NO_2$, on the other hand, since the sensitivity output characteristics with respect to NO and $NO_2$ are opposite in polarity, under an atmosphere in which both NO and $NO_2$ coexist, it has not been possible to correctly measure the concentration of NO or $NO_2$.

In the sensor described in Japanese Laid-Open Patent Publication No. 2009-511859 (PCT), it is difficult to accurately measure an $NH_3$ concentration over a prolonged time period, due to the instability of the oxide semiconductor electrode within the exhaust gas, and the weak adhesion strength with the substrate.

The present invention has been devised taking into consideration the aforementioned problems, and has the object of providing a gas sensor and a method of measuring concentrations of a plurality of target components in a gas to be measured, in which it is possible to accurately measure over a prolonged time period the concentration of a non-combusted component such as exhaust gas, and a plurality of components (for example, NO, $NO_2$, and $NH_3$) that coexist in the presence of oxygen.

[1] A gas sensor according to a first aspect of the present invention includes a sensor element having a structural body made up from a solid electrolyte that exhibits at least oxygen ion conductivity, a gas introduction port formed in the structural body and into which a gas to be measured is introduced, an oxygen concentration adjustment chamber formed in the structural body and communicating with the gas introduction port, and a measurement chamber formed in the structural body and communicating with the oxygen concentration adjustment chamber, an oxygen concentration control unit adapted to control the oxygen concentration in the oxygen concentration adjustment chamber, a temperature control unit adapted to control a temperature of the sensor element, and a specified component measurement unit adapted to measure a concentration of a specified component in the measurement chamber, the gas sensor further comprising a preliminary adjustment chamber provided within the structural body between the gas introduction port and the oxygen concentration adjustment chamber, and communicating with the gas introduction port, a preliminary oxygen concentration control unit adapted to control the oxygen concentration inside the preliminary adjustment chamber, a drive control unit adapted to control driving and stopping of the preliminary oxygen concentration control unit, and a target component acquisition unit adapted to acquire concentrations of a first target component and a second target component, on the basis of a difference between a sensor output from the specified component measurement unit at a time that the preliminary oxygen concentration control unit is driven, and a sensor output from the specified component measurement unit at a time that the preliminary oxygen concentration control unit is stopped, and one of the respective sensor outputs.

[2] In the first aspect of the present invention, the sensor element may comprise a first diffusion rate control member between the gas introduction port and the preliminary adjustment chamber, a second diffusion rate control member between the preliminary adjustment chamber and the oxygen concentration adjustment chamber, and a third diffusion rate control member between the oxygen concentration adjustment chamber and the measurement chamber.

[3] In the first aspect of the present invention, the oxygen concentration adjustment chamber may include a main adjustment chamber communicating with the preliminary adjustment chamber, and an auxiliary adjustment chamber communicating with the main adjustment chamber, and the measurement chamber may communicate with the auxiliary adjustment chamber.

[4] In this case, there may further be included a fourth diffusion rate control member between the main adjustment chamber and the auxiliary adjustment chamber.

[5] In the first aspect of the invention, a pump electrode may be included inside the oxygen concentration adjustment chamber, a measurement electrode may be included inside the measurement chamber, and the pump electrode preferably is constituted by a material having a catalytic activity lower than that of the measurement electrode.

[6] In the first aspect of the present invention, the specified component may be NO, the first target component may be NO, and the second target component may be $NH_3$.

[7] In this case, the preliminary oxygen concentration control unit, at a time of being driven, controls the oxygen concentration inside the preliminary adjustment chamber under a condition in which $NH_3$ is oxidized, without causing decomposition of NO inside the preliminary adjustment chamber.

[8] In either of aspects [6] or [7], the target component acquisition unit may utilize a first map. In the first map, there is recorded a relationship, which is measured experimentally in advance, between the NO concentration and the $NH_3$ concentration respectively for each of points specified by the sensor output from the specified component measurement unit at a time of stopping the preliminary oxygen concentration control unit, and a difference in the sensor outputs from the specified component measurement unit at times of driving and stopping the preliminary oxygen concentration control unit. The target component acquisition unit obtains the respective concentrations of NO and $NH_3$ by comparing with the first map the sensor output from the specified component measurement unit at the time of stopping the preliminary oxygen concentration control unit during actual use, and the difference in the sensor outputs from the specified component measurement unit at the times of driving and stopping the preliminary oxygen concentration control unit.

[9] In either of aspects [6] or [7], the target component acquisition unit may obtain the NO concentration in the following manner. More specifically, the target component acquisition unit obtains the $NH_3$ concentration corresponding to a difference in the sensor outputs from the specified component measurement unit at times of driving and stopping the preliminary oxygen concentration control unit during actual use, on the basis of a relationship, which is measured experimentally in advance, between the $NH_3$ concentration and the difference in the sensor outputs from the specified component measurement unit at the times of driving and stopping the preliminary oxygen concentration control unit. In addition, the target component acquisition unit may obtain the NO concentration by an operation of subtracting the $NH_3$ concentration, which was obtained beforehand from the difference in the sensor outputs, from a total NO concentration in which all of the concentrations of NO and $NH_3$ obtained from the sensor output at a time of stopping the preliminary oxygen concentration control unit are converted into NO.

[10] In the first aspect of the present invention, the specified component may be NO, the first target component may be NO, and the second target component may be $NO_2$.

[11] In this case, at a time of being driven, the preliminary oxygen concentration control unit controls the oxygen concentration inside the preliminary adjustment chamber under a condition in which $NO_2$ is converted into NO, without causing decomposition of NO inside the preliminary adjustment chamber.

[12] In either of aspects [10] or [11], the target component acquisition unit may utilize a second map. In the second map, there is recorded a relationship, which is measured experimentally in advance, between the NO concentration and the $NO_2$ concentration respectively for each of points specified by the sensor output from the specified component measurement unit at a time of stopping the preliminary oxygen concentration control unit, and a difference in the sensor outputs from the specified component measurement unit at times of driving and stopping the preliminary oxygen concentration control unit. The target component acquisition unit obtains the respective concentrations of NO and $NO_2$ by comparing with the second map the sensor output from the specified component measurement unit at the time of stopping the preliminary oxygen concentration control unit during actual use, and the difference in the sensor outputs from the specified component measurement unit at the times of driving and stopping the preliminary oxygen concentration control unit.

[13] In either of aspects [10] or [11], the target component acquisition unit may obtain the NO concentration in the following manner. More specifically, the target component acquisition unit obtains the $NO_2$ concentration corresponding to a difference in the sensor outputs from the specified component measurement unit at times of driving and stopping the preliminary oxygen concentration control unit during actual use, on the basis of a relationship, which is measured experimentally in advance, between the $NO_2$ concentration and the difference in the sensor outputs from the specified component measurement unit at the times of driving and stopping the preliminary oxygen concentration control unit. In addition, the target component acquisition unit may obtain the NO concentration by an operation of subtracting the $NO_2$ concentration, which was obtained beforehand from the difference in the sensor outputs, from a total NO concentration in which all of the concentrations of NO and $NO_2$ obtained from the sensor output at a time of stopping the preliminary oxygen concentration control unit are converted into NO.

[14] In a method of measuring concentrations of a plurality of target components in a gas to be measured according to a second aspect of the present invention, in which there is used a sensor element having a structural body made up from a solid electrolyte that exhibits at least oxygen ion conductivity, a gas introduction port formed in the structural body and into which a gas to be measured is introduced, an oxygen concentration adjustment chamber formed in the structural body and communicating with the gas introduction port, an oxygen concentration control unit adapted to control the oxygen concentration in the oxygen concentration adjustment chamber, a measurement chamber formed in the structural body and communicating with the oxygen concentration adjustment chamber, a preliminary adjustment chamber provided within the structural body between the gas introduction port and the oxygen concentration adjustment chamber, and communicating with the gas introduction port, a preliminary oxygen concentration control unit adapted to control the oxygen concentration inside the preliminary adjustment chamber, and a specified component measurement unit adapted to measure a concentration of a specified component in the measurement chamber, the method comprising a drive control step of controlling driving and stopping of the preliminary oxygen concentration control unit, and a target component acquisition step of acquiring concentrations of a first target component and a second target component, on the basis of a difference between a sensor output from the specified component measurement unit at a time that the preliminary oxygen concentration control unit is driven, and a sensor output from the specified component measurement unit at a time that the preliminary oxygen concentration control unit is stopped, and one of the respective sensor outputs.

[15] In the second aspect of the present invention, the specified component may be NO, the first target component may be NO, and the second target component may be $NH_3$.

[16] In this case, the preliminary oxygen concentration control unit, at a time of being driven, controls the oxygen concentration inside the preliminary adjustment chamber under a condition in which $NH_3$ is oxidized, without causing decomposition of NO inside the preliminary adjustment chamber.

[17] In either of aspects [15] or [16], in the target component acquisition step, a first map may be utilized. In the first map, there is recorded a relationship, which is measured experimentally in advance, between the NO concentration and the $NH_3$ concentration respectively for each of points specified by the sensor output from the specified component measurement unit at a time of stopping the preliminary oxygen concentration control unit, and a difference in the sensor outputs from the specified component measurement unit at times of driving and stopping the preliminary oxygen concentration control unit. In the target component acquisition step, the respective concentrations of NO and $NH_3$ may be obtained by comparing with the first map the sensor output from the specified component measurement unit at the time of stopping the preliminary oxygen concentration control unit during actual use, and the difference in the sensor outputs from the specified component measurement unit at the times of driving and stopping the preliminary oxygen concentration control unit.

[18] In either of aspects [15] or [16], in the target component acquisition step, the NO concentration may be obtained in the following manner. More specifically, in the target component acquisition step, the $NH_3$ concentration is obtained corresponding to a difference in the sensor outputs from the specified component measurement unit at times of driving and stopping the preliminary oxygen concentration control unit during actual use, on the basis of a relationship, which is measured experimentally in advance, between the $NH_3$ concentration and the difference in the sensor outputs from the specified component measurement unit at the times of driving and stopping the preliminary oxygen concentration control unit. In addition, in the target component acquisition step, the NO concentration may be obtained by an operation of subtracting the $NH_3$ concentration, which was obtained beforehand from the difference in the sensor outputs, from a total NO concentration in which all of the concentrations of NO and $NH_3$ obtained from the sensor output at a time of stopping the preliminary oxygen concentration control unit are converted into NO.

[19] In the second aspect of the present invention, the specified component may be NO, the first target component may be NO, and the second target component may be $NO_2$.

[20] In this case, at a time of being driven, the preliminary oxygen concentration control unit controls the oxygen concentration inside the preliminary adjustment chamber under a condition in which $NO_2$ is converted into NO, without causing decomposition of NO inside the preliminary adjustment chamber.

[21] In either of aspects [19] or [20], in the target component acquisition step, a second map may be utilized. In the second map, there is recorded a relationship, which is measured experimentally in advance, between the NO concentration and the $NO_2$ concentration respectively for each of points specified by the sensor output from the specified component measurement unit at a time of stopping the preliminary oxygen concentration control unit, and a difference in the sensor outputs from the specified component measurement unit at times of driving and stopping the preliminary oxygen concentration control unit. In the target component acquisition step, the respective concentrations of NO and $NO_2$ are obtained by comparing with the second map the sensor output from the specified component measurement unit at the time of stopping the preliminary oxygen concentration control unit during actual use, and the difference in the sensor outputs from the specified component measurement unit at the times of driving and stopping the preliminary oxygen concentration control unit.

[22] In either of aspects [19] or [20], in the target component acquisition step, the NO concentration may be obtained in the following manner. More specifically, in the target component acquisition step, the $NO_2$ concentration is obtained corresponding to a difference in the sensor outputs from the specified component measurement unit at times of driving and stopping the preliminary oxygen concentration control unit during actual use, on the basis of a relationship, which is measured experimentally in advance, between the $NO_2$ concentration and the difference in the sensor outputs from the specified component measurement unit at the times of driving and stopping the preliminary oxygen concentration control unit. In addition, in the target component acquisition step, the NO concentration may be obtained by an operation of subtracting the $NO_2$ concentration, which was obtained beforehand from the difference in the sensor outputs, from a total NO concentration in which all of the concentrations of NO and $NO_2$ obtained from the sensor output at a time of stopping the preliminary oxygen concentration control unit are converted into NO.

In accordance with the gas sensor and the method of measuring concentrations of a plurality of target components in a gas to be measured according to the present invention, it is possible to accurately measure over a prolonged time period the concentration of a non-combusted component such as exhaust gas, and a plurality of components (for example, NO, $NO_2$, and $NH_3$) that coexist in the presence of oxygen.

BRIEF DESCRIPTION OF DRAWINGS

FIG. 6 is an explanatory diagram showing the first map utilized by the first gas sensor in the form of a table;

FIG. 12 is an explanatory diagram showing the second map utilized by the second gas sensor in the form of a table;

FIG. 18A is a graph showing changes in NO output accompanying an elapse of time;

FIG. 18B is a graph showing changes in $NH_3$ output accompanying an elapse of time;

FIG. 18C is a graph showing changes in a degree of opening of a urea injector accompanying an elapse of time;

FIG. 20 is a cross-sectional view showing a structural example of a modified example of the first gas sensor and the second gas sensor.

DESCRIPTION OF EMBODIMENTS

Embodiments of a gas sensor according to the present invention, and a method for measuring concentrations of a plurality of target components in a gas to be measured will be presented and described below with reference to FIGS. 1 to 20. In the present specification, the term "to" when used to indicate a numerical range is used with the implication of including the numerical values written before and after the term as a lower limit value and an upper limit value of the numerical range.

Figure 1:
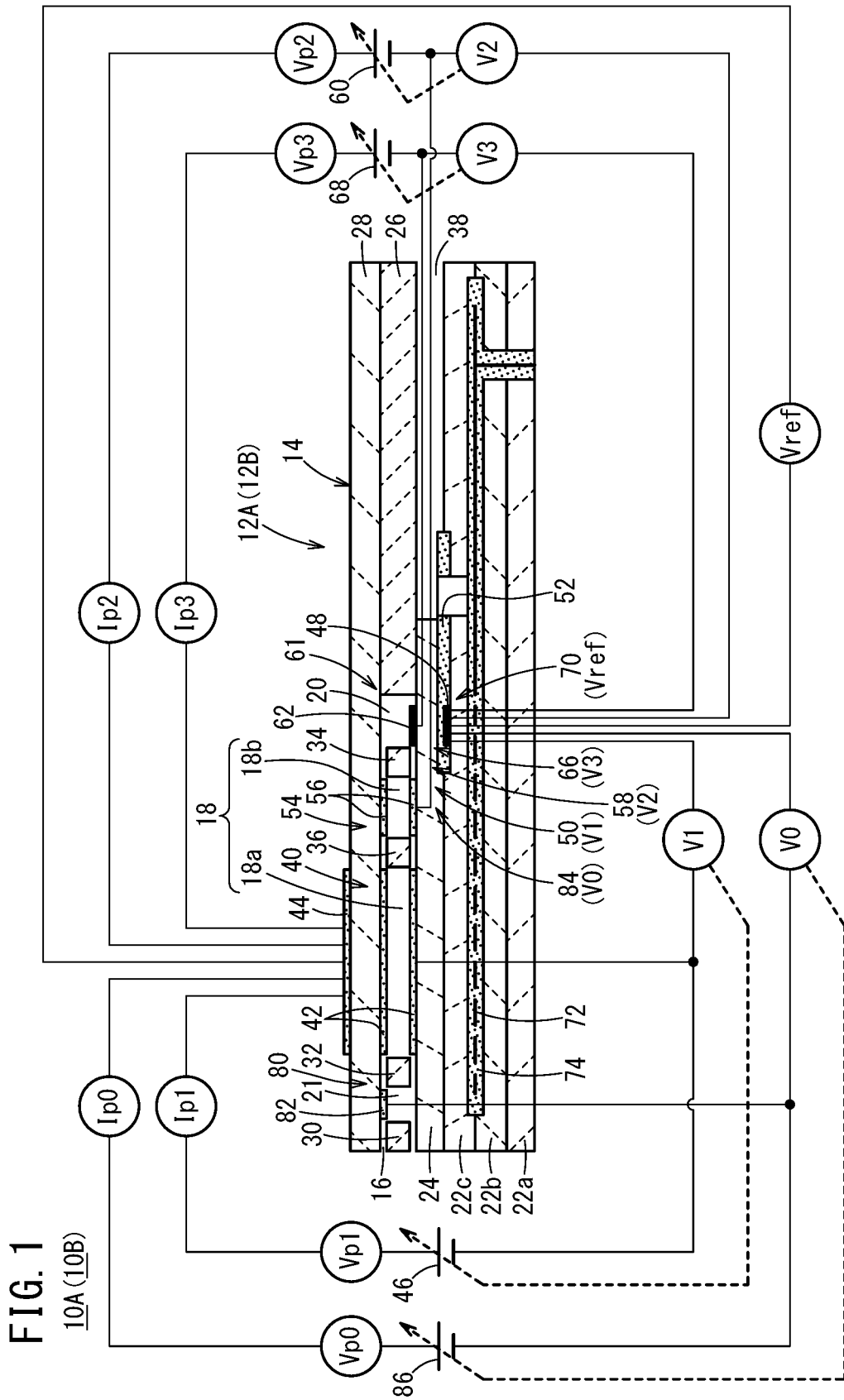
FIG. 1 is a cross-sectional view in which there is shown one structural example of a gas sensor (first gas sensor) according to a first embodiment and a gas sensor (second gas sensor) according to a second embodiment.
Figure 2:
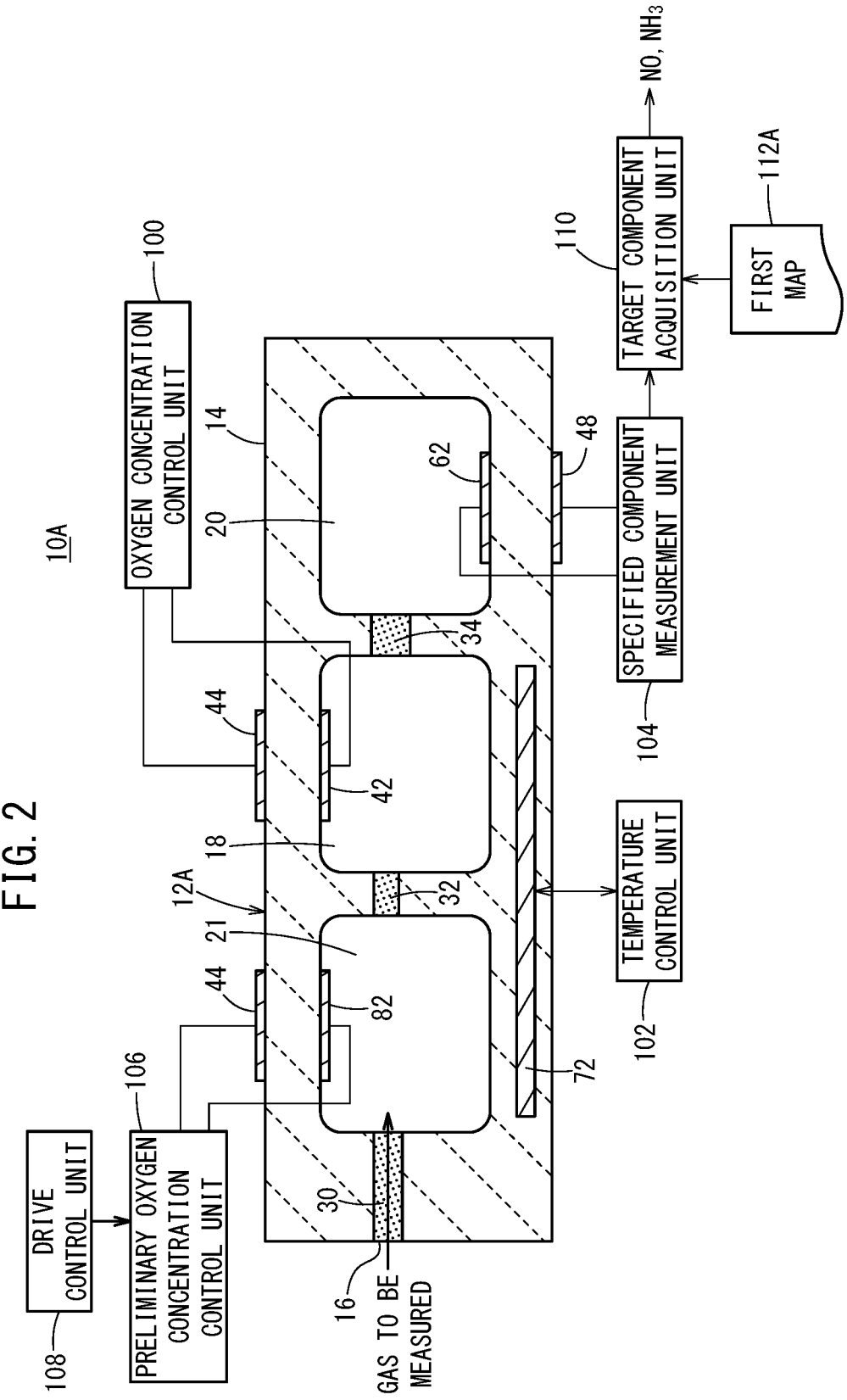
FIG. 2 is a configuration diagram schematically showing a first gas sensor.

First, as shown in FIGS. 1 and 2, a gas sensor (hereinafter referred to as a first gas sensor 10A) according to a first embodiment includes a first sensor element 12A. The first sensor element 12A includes a structural body 14 made up from a solid electrolyte that exhibits at least oxygen ion conductivity, a gas introduction port 16 formed in the structural body 14 and into which a gas to be measured is introduced, an oxygen concentration adjustment chamber 18 formed in the structural body 14 and communicating with the gas introduction port 16, and a measurement chamber 20 formed in the structural body 14 and communicating with the oxygen concentration adjustment chamber 18.

The oxygen concentration adjustment chamber 18 includes a main adjustment chamber 18a communicating with the gas introduction port 16, and an auxiliary adjustment chamber 18b communicating with the main adjustment chamber 18a. The measurement chamber 20 communicates with the auxiliary adjustment chamber 18b.

Furthermore, the first gas sensor 10A includes a preliminary adjustment chamber 21 provided between the gas introduction port 16 and the main adjustment chamber 18a within the structural body 14, and which communicates with the gas introduction port 16.

More specifically, the structural body 14 of the first sensor element 12A is constituted by six layers including a first substrate layer 22a, a second substrate layer 22b, a third substrate layer 22c, a first solid electrolyte layer 24, a spacer layer 26, and a second solid electrolyte layer 28, which are stacked in this order from a lower side as viewed in the drawing. The respective layers are composed respectively of an oxygen ion conductive solid electrolyte layer such as zirconia ($ZrO_2$) or the like.

Between a lower surface of the second solid electrolyte layer 28 and an upper surface of the first solid electrolyte layer 24 on a distal end side of the first sensor element 12A, there are provided the gas introduction port 16, a first diffusion rate control portion 30, the preliminary adjustment chamber 21, a second diffusion rate control portion 32, the oxygen concentration adjustment chamber 18, a third diffusion rate control portion 34, and the measurement chamber 20. Further, a fourth diffusion rate control portion 36 is provided between the main adjustment chamber 18a and the auxiliary adjustment chamber 18b that make up the oxygen concentration adjustment chamber 18.

The gas introduction port 16, the first diffusion rate control portion 30, the preliminary adjustment chamber 21, the second diffusion rate control portion 32, the main adjustment chamber 18a, the fourth diffusion rate control portion 36, the auxiliary adjustment chamber 18b, the third diffusion rate control portion 34, and the measurement chamber 20 are formed adjacent to each other in a manner communicating in this order. The portion from the gas introduction port 16 leading to the measurement chamber 20 is also referred to as a gas flow section.

The gas introduction port 16, the preliminary adjustment chamber 21, the main adjustment chamber 18a, the auxiliary adjustment chamber 18b, and the measurement chamber 20 are internal spaces provided by hollowing out the spacer layer 26. Any of the preliminary adjustment chamber 21, the main adjustment chamber 18a, the auxiliary adjustment chamber 18b, and the measurement chamber 20 is arranged in a manner so that respective upper parts thereof are defined by a lower surface of the second solid electrolyte layer 28, respective lower parts thereof are defined by an upper surface of the first solid electrolyte layer 24, and respective side parts thereof are defined by side surfaces of the spacer layer 26.

Any of the first diffusion rate control portion 30, the third diffusion rate control portion 34, and the fourth diffusion rate control portion 36 is provided as two horizontally elongated slits (in which openings thereof have a longitudinal direction in a direction perpendicular to the drawing). The second diffusion rate control portion 32 is provided as one horizontally elongated slit (in which an opening thereof has a longitudinal direction in a direction perpendicular to the drawing).

Further, a reference gas introduction space 38 is disposed between an upper surface of the third substrate layer 22c and a lower surface of the spacer layer 26, at a position that is farther from the distal end side than the gas flow section. The reference gas introduction space 38 is an internal space in which an upper part thereof is defined by a lower surface of the spacer layer 26, a lower part thereof is defined by an upper surface of the third substrate layer 22c, and a side part thereof is defined by a side surface of the first solid electrolyte layer 24. For example, oxygen or atmospheric air is introduced as a reference gas into the reference gas introduction space 38.

The gas introduction port 16 is a location that opens with respect to the external space, and the target gas to be measured is drawn into the first sensor element 12A from the external space through the gas introduction port 16.

The first diffusion rate control portion 30 is a location that imparts a predetermined diffusion resistance to the gas to be measured which is introduced from the gas introduction port 16 into the preliminary adjustment chamber 21. Details concerning the preliminary adjustment chamber 21 will be described later.

The second diffusion rate control portion 32 is a location that imparts a predetermined diffusion resistance to the gas to be measured which is introduced from the preliminary adjustment chamber 21 into the main adjustment chamber 18a.

The main adjustment chamber 18a is provided as a space for the purpose of adjusting an oxygen partial pressure within the gas to be measured that is introduced from the gas introduction port 16. The oxygen partial pressure is adjusted by operation of a main pump cell 40.

The main pump cell 40 comprises an electrochemical pump cell (main electrochemical pumping cell), which is constituted by a main interior side pump electrode 42, an exterior side pump electrode 44, and an oxygen ion conductive solid electrolyte which is sandwiched between the two pump electrodes. The main interior side pump electrode 42 is provided substantially over the entire surface of an upper surface of the first solid electrolyte layer 24, a lower surface of the second solid electrolyte layer 28, and side surfaces of the spacer layer 26 that define the main adjustment chamber 18a. The exterior side pump electrode 44 is provided in a condition of being exposed to the external space in a region corresponding to the main interior side pump electrode 42 on the upper surface of the second solid electrolyte layer 28. The main interior side pump electrode 42 and the exterior side pump electrode 44 are made of a material that weakens the reduction capability with respect to the NOx component within the gas to be measured. For example, the pump electrodes are formed as porous cermet electrodes (for example, cermet electrodes of $ZrO_2$ and a noble metal such as Pt, containing 0.1 to 30.0 wt % of Au) having rectangular shapes as viewed in plan.

The main pump cell 40 applies a first pump voltage Vp1 supplied from a first variable power source 46 which is provided externally of the first sensor element 12A, and by allowing a first pump current Ip1 to flow between the exterior side pump electrode 44 and the main interior side pump electrode 42, it is possible to pump oxygen in the interior of the main adjustment chamber 18a into the external space, or alternatively, to pump oxygen in the external space into the main adjustment chamber 18a.

Further, the first sensor element 12A includes a first oxygen partial pressure detecting sensor cell 50 which is an electrochemical sensor cell. The first oxygen partial pressure detecting sensor cell 50 is constituted by the main interior side pump electrode 42, a reference electrode 48 sandwiched between the first solid electrolyte layer 24 and an upper surface of the third substrate layer 22c, and an oxygen ion conductive solid electrolyte sandwiched between these electrodes. The reference electrode 48 is an electrode having a substantially rectangular shape as viewed in plan, which is made from a porous cermet in the same manner as the exterior side pump electrode 44 and the like. Further, around the periphery of the reference electrode 48, a reference gas introduction layer 52 is provided, which is made from porous alumina and is connected to the reference gas introduction space 38. More specifically, the reference gas in the reference gas introduction space 38 is introduced to the surface of the reference electrode 48 via the reference gas introduction layer 52. The first oxygen partial pressure detecting sensor cell 50 generates a first electromotive force V1 between the main interior side pump electrode 42 and the reference electrode 48, which is caused by the difference in oxygen concentration between the atmosphere inside the main adjustment chamber 18a and the reference gas in the reference gas introduction space 38.

The first electromotive force V1 generated in the first oxygen partial pressure detecting sensor cell 50 changes depending on the oxygen partial pressure of the atmosphere existing in the main adjustment chamber 18a. In accordance with the first electromotive force V1, the first sensor element 12A feedback-controls the first variable power source 46 of the main pump cell 40. Consequently, the first pump voltage Vp1, which is applied by the first variable power source 46 to the main pump cell 40, can be controlled in accordance with the oxygen partial pressure of the atmosphere in the main adjustment chamber 18a.

The fourth diffusion rate control portion 36 imparts a predetermined diffusion resistance to the gas to be measured, the oxygen concentration (oxygen partial pressure) of which is controlled by operation of the main pump cell 40 in the main adjustment chamber 18a, and is a location that guides the gas to be measured into the auxiliary adjustment chamber 18b.

The auxiliary adjustment chamber 18b is provided as a space for further carrying out adjustment of the oxygen partial pressure by an auxiliary pump cell 54, with respect to the gas to be measured which is introduced through the fourth diffusion rate control portion 36, after the oxygen concentration (oxygen partial pressure) has been adjusted beforehand in the main adjustment chamber 18a. In accordance with this feature, the oxygen concentration inside the auxiliary adjustment chamber 18b can be kept constant with high accuracy, and therefore, the first gas sensor 10A is made capable of measuring the NOx concentration with high accuracy.

The auxiliary pump cell 54 is an electrochemical pump cell, and is constituted by an auxiliary pump electrode 56, which is provided substantially over the entirety of the lower surface of the second solid electrolyte layer 28 facing toward the auxiliary adjustment chamber 18b, the exterior side pump electrode 44, and the second solid electrolyte layer 28.

Moreover, in the same manner as the main interior side pump electrode 42, the auxiliary pump electrode 56 is also formed using a material that weakens the reduction capability with respect to the NOx component within the gas to be measured.

The auxiliary pump cell 54, by applying a desired second voltage Vp2 between the auxiliary pump electrode 56 and the exterior side pump electrode 44, is capable of pumping out oxygen within the atmosphere inside the auxiliary adjustment chamber 18b into the external space, or alternatively, is capable of pumping in oxygen from the external space into the auxiliary adjustment chamber 18b.

Further, in order to control the oxygen partial pressure within the atmosphere inside the auxiliary adjustment chamber 18b, an electrochemical sensor cell, and more specifically, a second oxygen partial pressure detecting sensor cell 58 for controlling the auxiliary pump, is constituted by the auxiliary pump electrode 56, the reference electrode 48, the second solid electrolyte layer 28, the spacer layer 26, and the first solid electrolyte layer 24.

Moreover, the auxiliary pump cell 54 carries out pumping by a second variable power source 60, the voltage of which is controlled based on a second electromotive force V2 detected by the second oxygen partial pressure detecting sensor cell 58. Consequently, the oxygen partial pressure within the atmosphere inside the auxiliary adjustment chamber 18b is controlled so as to become a low partial pressure that does not substantially influence the measurement of NOx.

Further, together therewith, a second pump current Ip2 of the auxiliary pump cell 54 is used so as to control the second electromotive force V2 of the second oxygen partial pressure detecting sensor cell 58. More specifically, the second pump current Ip2 is input as a control signal to the second oxygen partial pressure detecting sensor cell 58, and by controlling the second electromotive force V2, the gradient of the oxygen partial pressure within the gas to be measured, which is introduced through the fourth diffusion rate control portion 36 into the auxiliary adjustment chamber 18b, is controlled so as to remain constant at all times. When the first gas sensor 10A is used as an NOx sensor, by the actions of the main pump cell 40 and the auxiliary pump cell 54, the oxygen concentration inside the auxiliary adjustment chamber 18b is maintained at a predetermined value with high accuracy for each of the respective conditions.

The third diffusion rate control portion 34 imparts a predetermined diffusion resistance to the gas to be measured, the oxygen concentration (oxygen partial pressure) of which is controlled by operation of the auxiliary pump cell 54 in the auxiliary adjustment chamber 18b, and is a location that guides the gas to be measured into the measurement chamber 20.

Measurement of the NOx concentration is primarily performed by operations of a measurement pump cell 61 provided in the measurement chamber 20. The measurement pump cell 61 is an electrochemical pump cell constituted by a measurement electrode 62, the exterior side pump electrode 44, the second solid electrolyte layer 28, the spacer layer 26, and the first solid electrolyte layer 24. The measurement electrode 62 is provided, for example, directly on the upper surface of the first solid electrolyte layer 24 inside the measurement chamber 20, and is a porous cermet electrode made of a material whose reduction capability with respect to the NOx component within the gas to be measured is higher than that of the main interior side pump electrode 42. The measurement electrode 62 also functions as an NOx reduction catalyst for reducing NOx existing within the atmosphere above the measurement electrode 62.

The measurement pump cell 61 is capable of pumping out oxygen that is generated by the decomposition of nitrogen oxide within the atmosphere around the periphery of the measurement electrode 62 (inside the measurement chamber 20), and can detect the generated amount as a measurement pump current Ip3, or stated otherwise, as the sensor output.

Further, in order to detect the oxygen partial pressure around the periphery of the measurement electrode 62 (inside the measurement chamber 20), an electrochemical sensor cell, and more specifically, a third oxygen partial pressure detecting sensor cell 66 for controlling the measurement pump, is constituted by the first solid electrolyte layer 24, the measurement electrode 62, and the reference electrode 48. A third variable power source 68 is controlled based on a third electromotive force V3 detected by the third oxygen partial pressure detecting sensor cell 66.

The gas to be measured, which is introduced into the auxiliary adjustment chamber 18b, reaches the measurement electrode 62 inside the measurement chamber 20 through the third diffusion rate control portion 34, under a condition in which the oxygen partial pressure is controlled. Nitrogen oxide existing within the gas to be measured around the periphery of the measurement electrode 62 is reduced to thereby generate oxygen. Then, the generated oxygen is subjected to pumping by the measurement pump cell 61. At this time, a third voltage Vp3 of the third variable power source 68 is controlled in a manner so that the third electromotive force V3 detected by the third oxygen partial pressure detecting sensor cell 66 becomes constant. The amount of oxygen generated around the periphery of the measurement electrode 62 is proportional to the concentration of nitrogen oxide within the gas to be measured. Accordingly, the nitrogen oxide concentration within the gas to be measured can be calculated using the measurement pump current Ip3 of the measurement pump cell 61. More specifically, the measurement pump cell 61 constitutes a specified component measurement unit for measuring the concentration of a specified component (NO) in the measurement chamber 20.

Further, the first gas sensor 10A includes an electrochemical sensor cell 70. The sensor cell 70 includes the second solid electrolyte layer 28, the spacer layer 26, the first solid electrolyte layer 24, the third substrate layer 22c, the exterior side pump electrode 44, and the reference electrode 48. In accordance with the electromotive force Vref obtained by the sensor cell 70, it is possible to detect the oxygen partial pressure within the gas to be measured existing externally of the sensor.

Furthermore, in the first sensor element 12A, a heater 72 is formed in a manner of being sandwiched from above and below between the second substrate layer 22b and the third substrate layer 22c. The heater 72 generates heat by being supplied with power from the exterior through a non-illustrated heater electrode provided on a lower surface of the first substrate layer 22a. As a result of the heat generated by the heater 72, the oxygen ion conductivity of the solid electrolyte that constitutes the first sensor element 12A is enhanced. The heater 72 is embedded over the entire region of the preliminary adjustment chamber 21 and the oxygen concentration adjustment chamber 18, and a predetermined location of the first sensor element 12A can be heated and maintained at a predetermined temperature. Moreover, a heater insulating layer 74 made of alumina or the like is formed on upper and lower surfaces of the heater 72, for the purpose of obtaining electrical insulation thereof from the second substrate layer 22b and the third substrate layer 22c (hereinafter, the heater 72, the heater electrode, and the heater insulating layer 74 may also be referred to collectively as a heater portion).

In addition, the preliminary adjustment chamber 21 is driven by a later-described drive control unit 108 (see FIG. 2), and during driving thereof, functions as a space for adjusting the oxygen partial pressure within the gas to be measured which is introduced from the gas introduction port 16. The oxygen partial pressure is adjusted by operation of a preliminary pump cell 80.

The preliminary pump cell 80 is a preliminary electrochemical pump cell, and is constituted by a preliminary pump electrode 82, which is provided substantially over the entirety of the lower surface of the second solid electrolyte layer 28 facing toward the preliminary adjustment chamber 21, the exterior side pump electrode 44, and the second solid electrolyte layer 28.

Moreover, in the same manner as the main interior side pump electrode 42, the preliminary pump electrode 82 is also formed using a material that weakens the reduction capability with respect to the NOx component within the gas to be measured.

The preliminary pump cell 80, by applying a desired preliminary voltage Vp0 between the preliminary pump electrode 82 and the exterior side pump electrode 44, is capable of pumping out oxygen within the atmosphere inside the preliminary adjustment chamber 21 into the external space, or alternatively, is capable of pumping in oxygen from the external space into the preliminary adjustment chamber 21.

Further, the first gas sensor 10A includes a preliminary oxygen partial pressure detecting sensor cell 84 for controlling the preliminary pump, in order to control the oxygen partial pressure within the atmosphere inside the preliminary adjustment chamber 21. The sensor cell 84 includes the preliminary pump electrode 82, the reference electrode 48, the second solid electrolyte layer 28, the spacer layer 26, and the first solid electrolyte layer 24.

Moreover, the preliminary pump cell 80 carries out pumping by a preliminary variable power source 86, the voltage of which is controlled based on a preliminary electromotive force V0 detected by the preliminary oxygen partial pressure detecting sensor cell 84. Consequently, the oxygen partial pressure within the atmosphere inside the preliminary adjustment chamber 21 is controlled so as to become a low partial pressure that does not substantially influence the measurement of NOx.

Further, together therewith, a preliminary pump current Ip0 thereof is used so as to control the electromotive force of the preliminary oxygen partial pressure detecting sensor cell 84. More specifically, the preliminary pump current Ip0 is input as a control signal to the preliminary oxygen partial pressure detecting sensor cell 84, and by controlling the preliminary electromotive force V0, the gradient of the oxygen partial pressure within the gas to be measured, which is introduced from the first diffusion rate control portion 30 into the preliminary adjustment chamber 21, is controlled so as to remain constant at all times.

The preliminary adjustment chamber 21 also functions as a buffer space. More specifically, it is possible to cancel fluctuations in the concentration of the gas to be measured, which are caused by pressure fluctuations of the gas to be measured in the external space (pulsations in the exhaust pressure, in the case that the gas to be measured is an exhaust gas of an automobile).

Furthermore, as shown schematically in FIG. 2, the first gas sensor 10A includes an oxygen concentration control unit 100 that controls the oxygen concentration inside the oxygen concentration adjustment chamber 18, a temperature control unit 102 that controls the temperature of the first sensor element 12A, a specified component measurement unit 104 that measures the concentration of a specified component (NO) inside the measurement chamber 20, a preliminary oxygen concentration control unit 106, a drive control unit 108, and a target component acquisition unit 110.

Moreover, the oxygen concentration control unit 100, the temperature control unit 102, the specified component measurement unit 104, the preliminary oxygen concentration control unit 106, the drive control unit 108, and the target component acquisition unit 110 are constituted by one or more electronic circuits having, for example, one or a plurality of CPUs (central processing units), memory devices, and the like. The electronic circuits are software-based functional units in which predetermined functions are realized, for example, by the CPUs executing programs stored in a storage device. Of course, the electronic circuits may be constituted by an integrated circuit such as an FPGA (Field-Programmable Gate Array), in which the plurality of electronic circuits are connected according to the functions thereof.

In the conventional technique, after having carried out conversion into NO with respect to all of the target components of NO and $NH_3$ existing inside the oxygen concentration adjustment chamber 18, the target components are introduced into the measurement chamber 20, and a total amount of the two components is measured. Stated otherwise, it has been impossible to measure the concentrations of each of the two target components, that is, the respective concentrations of NO and $NH_3$.

In contrast thereto, as described above, by being equipped with the preliminary adjustment chamber 21, the preliminary oxygen concentration control unit 106, the drive control unit 108, and the target component acquisition unit 110, in addition to the oxygen concentration adjustment chamber 18, the oxygen concentration control unit 100, the temperature control unit 102, and the specified component measurement unit 104, the first gas sensor 10A is made capable of measuring the respective concentrations of NO and $NH_3$.

On the basis of the preset oxygen concentration condition, and the first electromotive force V1 generated in the first oxygen partial pressure detecting sensor cell 50 (see FIG. 1), the oxygen concentration control unit 100 feedback-controls the first variable power source 46, thereby adjusting the oxygen concentration inside the oxygen concentration adjustment chamber 18 to a concentration in accordance with the above-described condition.

The temperature control unit 102 feedback-controls the heater 72 on the basis of a preset sensor temperature condition, and the measured value from a temperature sensor (not shown) that measures the temperature of the first sensor element 12A, whereby the temperature of the first sensor element 12A is adjusted to a temperature in accordance with the above-described condition.

By the oxygen concentration control unit 100 or the temperature control unit 102, or alternatively, by the oxygen concentration control unit 100 and the temperature control unit 102, the first gas sensor 10A performs a control so as to convert all of the $NH_3$ into NO, without causing decomposition of NO inside the oxygen concentration adjustment chamber 18.

On the basis of the preset oxygen concentration condition, and the preliminary electromotive force V0 generated in the preliminary oxygen partial pressure detecting sensor cell 84 (see FIG. 1), the preliminary oxygen concentration control unit 106 feedback-controls the preliminary variable power source 86, thereby adjusting the oxygen concentration inside the preliminary adjustment chamber 21 to a concentration in accordance with the condition.

By the preliminary oxygen concentration control unit 106, all of the $NH_3$ is converted into NO, without causing decomposition of NO inside the preliminary adjustment chamber 21.

The drive control unit 108 controls both driving and stopping of the preliminary oxygen concentration control unit 106. Consequently, the preliminary pump cell 80 is controlled so as to be turned on or off. During driving of the preliminary oxygen concentration control unit 106, the preliminary pump cell 80 is turned on, and therefore, all of the $NH_3$ inside the preliminary adjustment chamber 21 is converted into NO, and flows into the oxygen concentration adjustment chamber 18 through the second diffusion rate control portion 32. While the preliminary oxygen concentration control unit 106 is stopped, the preliminary pump cell 80 is turned off, and therefore, the $NH_3$ inside the preliminary adjustment chamber 21 is not converted into NO, but flows into the oxygen concentration adjustment chamber 18 through the second diffusion rate control portion 32.

The target component acquisition unit 110 acquires the respective concentrations of NO and $NH_3$ on the basis of the sensor output from the specified component measurement unit 104 at the time of driving the preliminary oxygen concentration control unit 106, and the difference in the sensor outputs from the specified component measurement unit 104 at the time of stopping the preliminary oxygen concentration control unit 106.

Next, processing operations of the first gas sensor 10A will be described with reference also to FIGS. 3 and 4.

Figure 3:
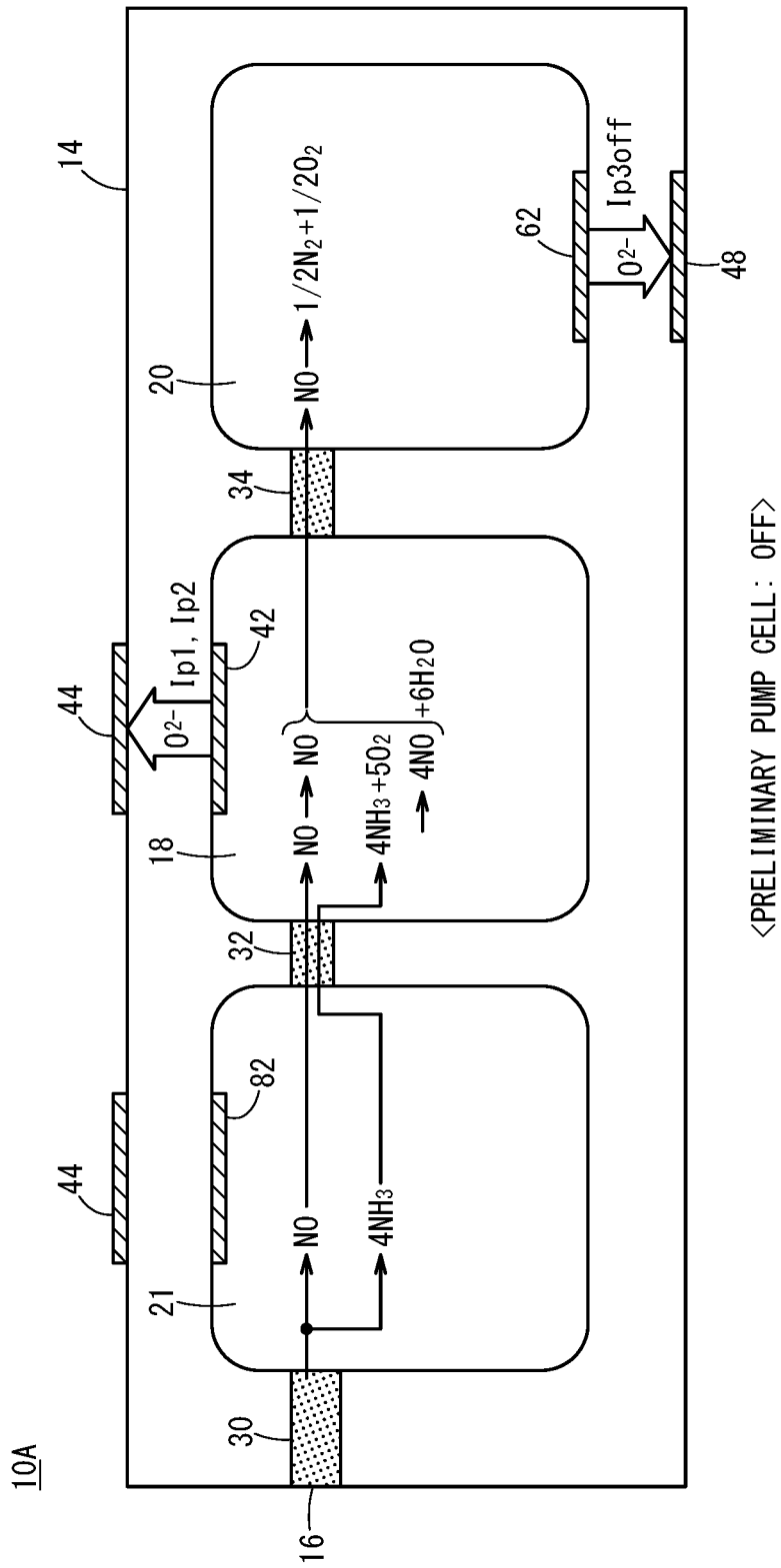
FIG. 3 is an explanatory diagram schematically showing reactions in a preliminary adjustment chamber, an oxygen concentration adjustment chamber, and a measurement chamber, for a case in which a preliminary pump cell is turned off in the first gas sensor.

First, as shown in FIG. 3, the $NH_3$ that was introduced through the gas introduction port 16 reaches the oxygen concentration adjustment chamber 18 during a period in which the preliminary oxygen concentration control unit 106 is stopped by the drive control unit 108. In the oxygen concentration adjustment chamber 18, by operation of the oxygen concentration control unit 100, a control is performed so as to convert all of the $NH_3$ into NO, and therefore, the $NH_3$ that has flowed into the oxygen concentration adjustment chamber 18 from the preliminary adjustment chamber 21 causes an oxidation reaction of $NH_3 \rightarrow NO$ to occur inside the oxygen concentration adjustment chamber 18, and all of the $NH_3$ inside the oxygen concentration adjustment chamber 18 is converted into NO. Accordingly, the $NH_3$ that was introduced through the gas introduction port 16 passes through the first diffusion rate control portion 30 and the second diffusion rate control portion 32 at a speed of the $NH_3$ diffusion coefficient of 2.2 $cm^2$/sec, and after being converted into NO inside the oxygen concentration adjustment chamber 18, passes through the third diffusion rate control portion 34 at a speed of the NO diffusion coefficient of 1.8 $cm^2$/sec, and moves into the adjacent measurement chamber 20.

Figure 4:
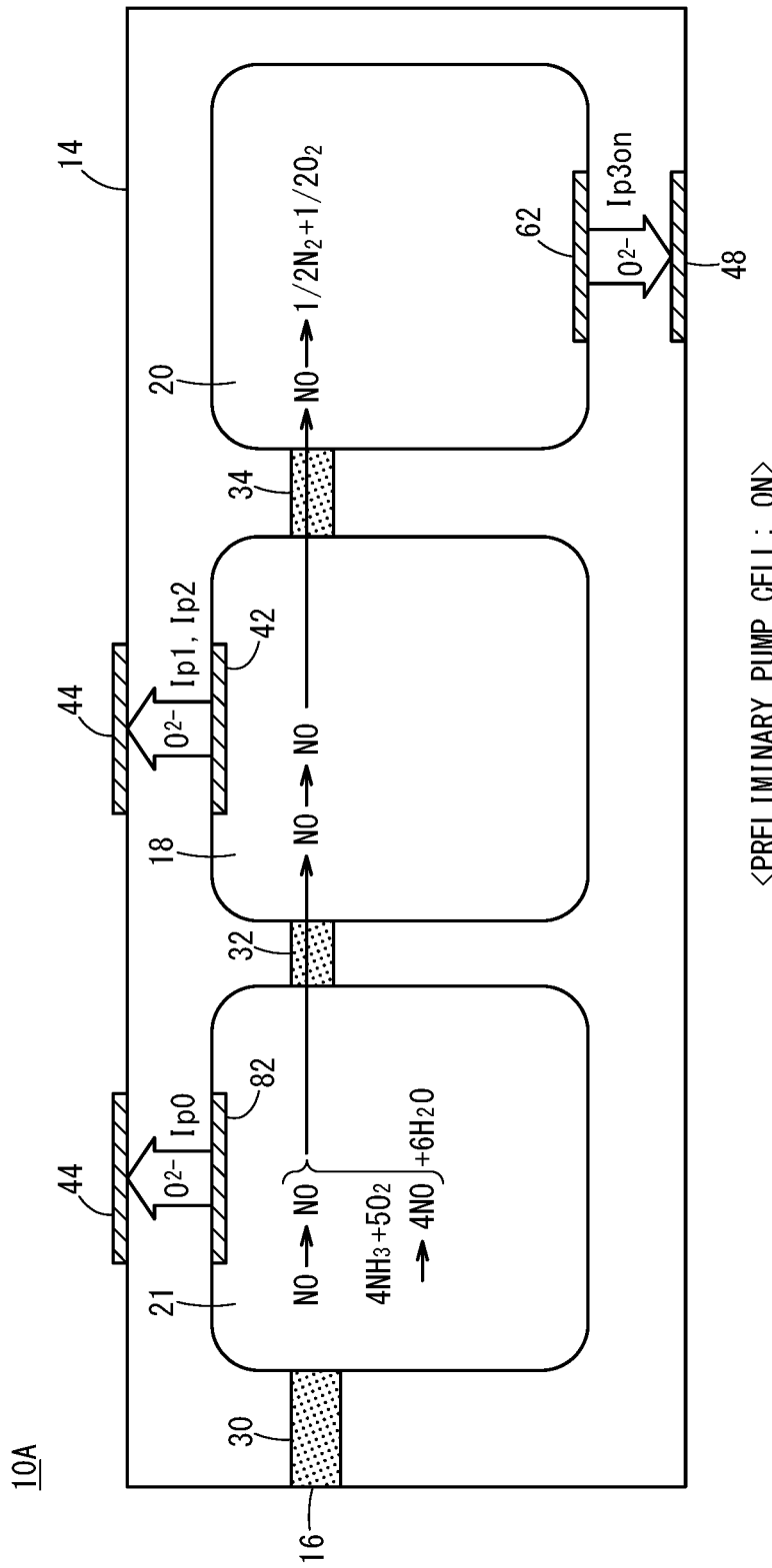
FIG. 4 is an explanatory diagram schematically showing reactions inside the preliminary adjustment chamber, the oxygen concentration adjustment chamber, and the measurement chamber, for a case in which the preliminary pump cell is turned on in the first gas sensor.

On the other hand, during a period in which the preliminary oxygen concentration control unit 106 is being driven by the drive control unit 108, as shown in FIG. 4, the oxidation reaction of $NH_3 \rightarrow NO$ occurs inside the preliminary adjustment chamber 21, and all of the $NH_3$ that was introduced through the gas introduction port 16 is converted into NO. Accordingly, although the $NH_3$ passes through the first diffusion rate control portion 30 at an $NH_3$ diffusion coefficient of 2.2 $cm^2$/sec, after having passed through the second diffusion rate control portion 32 on the innermost side from the preliminary adjustment chamber 21, movement into the measurement chamber 20 occurs at a speed of the NO diffusion coefficient of 1.8 $cm^2$/sec.

Stated otherwise, when the preliminary oxygen concentration control unit 106 is switched from a stopped state into a driven state, the location where the oxidation reaction of $NH_3$ takes place is moved from the oxygen concentration adjustment chamber 18 to the preliminary adjustment chamber 21.

The action of moving the location where the oxidation reaction of $NH_3$ takes place from the oxygen concentration adjustment chamber 18 to the preliminary adjustment chamber 21 implies that the state when the $NH_3$ in the gas to be measured passes through the second diffusion rate control portion 32 is equivalent to a state of being changed from $NH_3$ to NO. In addition, since NO and $NH_3$ possess different diffusion coefficients, the difference between passing through the second diffusion rate control portion 32 with NO or passing therethrough with $NH_3$ corresponds to a difference in the amount of NO that flows into the measurement chamber 20, and therefore, the measurement pump current Ip3 that flows to the measurement pump cell 61 is made to change.

In this case, the measurement pump current Ip3on when the preliminary pump cell 80 is turned on, and the amount of change $\Delta\Delta$Ip3 in the measurement pump current Ip3off when the preliminary pump cell 80 is turned off are uniquely determined by the concentration of $NH_3$ in the gas to be measured. Therefore, it is possible to calculate the concentrations of NO and $NH_3$ from the measurement pump current Ip3on or Ip3off when the preliminary pump cell 80 is turned on or off, and the amount of change $\Delta$Ip3 in the aforementioned measurement pump current Ip3.

Accordingly, with the target component acquisition unit 110, the respective concentrations of NO and $NH_3$ are acquired on the basis of the measurement pump current Ip3on when the preliminary pump cell 80 is turned on, the amount of change ΔIp3 between the measurement pump current Ip3on and the measurement pump current Ip3off when the preliminary pump cell 80 is turned off, and the first map 112A (see FIG. 2).

Figure 5:
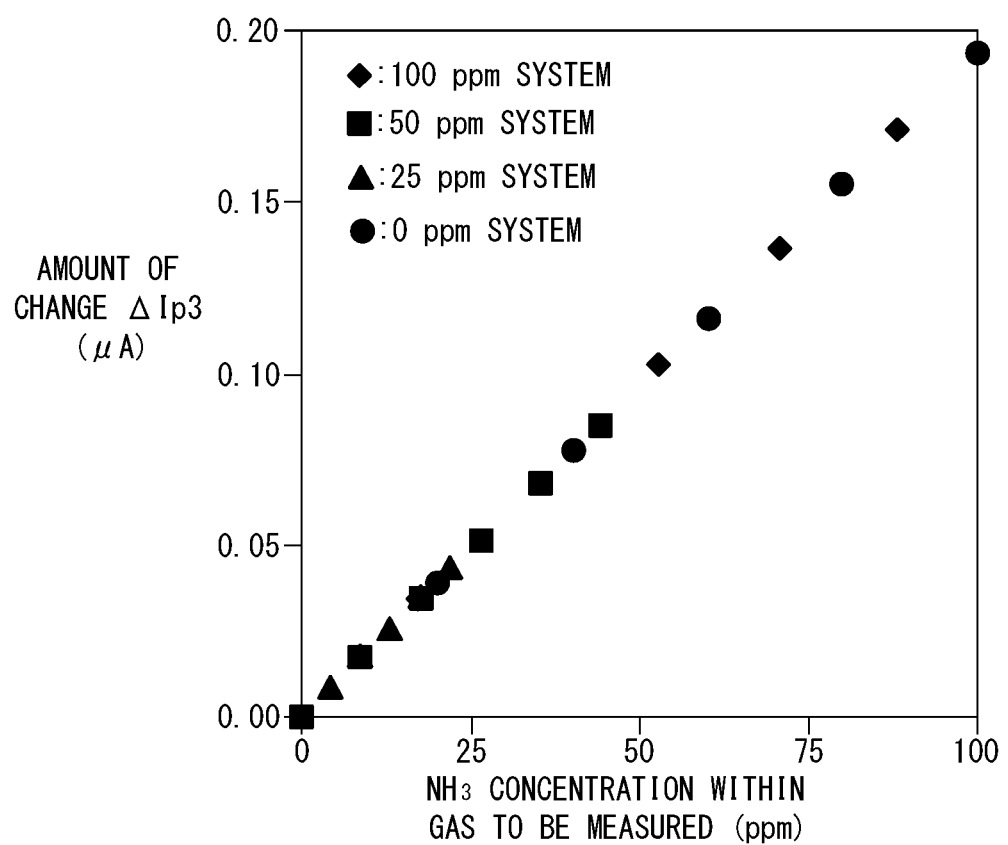
FIG. 5 is a view graphically showing a first map utilized by the first gas sensor.

When shown in the form of a graph, the first map 112A becomes a graph in which, as shown in FIG. 5, the $NH_3$ concentration (ppm) within the gas to be measured is set on the horizontal axis, and there is set on the vertical axis the difference, or in other words, the amount of change ΔIp3 between the measurement pump current Ip3on at a time that the preliminary pump cell 80 is turned on, and the measurement pump current Ip3off at a time that the preliminary pump cell 80 is turned off. In FIG. 5, there is shown representatively a graph in which the NO concentration converted values of the measurement pump current values, at the time that the preliminary pump cell 80 is turned off, are plotted as points pertaining to, for example, a 100 ppm system, a 50 ppm system, a 25 ppm system, and a 0 ppm system. When shown in the form of a table to facilitate understanding, the contents thereof are as shown in FIG. 6. These concentrations are obtained by experiment or by simulation.

As can be understood from FIG. 6, by using the first map 112A, and on the basis of the measurement pump current Ip3off when the preliminary pump cell 80 is turned off (i.e., a measurement pump current value similar to that of a conventional serial two-chamber type NOx sensor), any one of the 100 ppm system, the 50 ppm system, the 25 ppm system, and the 0 ppm system is determined and used to identify the respective concentrations of NO and $NH_3$ based on the amount of change ΔIp3.

More specifically, by specifying a point on the first map 112A from the measurement pump current Ip3off when the preliminary pump cell 80 is turned off, and the amount of change ΔIp3, it is possible to identify the NO concentration and the $NH_3$ concentration. For example, in the case that the measurement pump current Ip3off, which is similar to that of a conventional serial two-chamber type NOx sensor, is 2.137 µA, using the aforementioned serial two-chamber type NOx sensor, it could only be understood that the total concentrations of NO and $NH_3$ is approximately 100 ppm. However, in the first gas sensor 10A, by being combined with the amount of change ΔIp3, it is possible to individually specify the NO concentration and the $NH_3$ concentration, in a manner so that the NO concentration is 100 ppm and the $NH_3$ concentration is 0 ppm at point p1, the NO concentration is 80 ppm and the $NH_3$ concentration is 17.6 ppm at point p2, and the NO concentration is 60 ppm and the $NH_3$ concentration is 35.2 ppm at point p3. If there is no corresponding point on the first map 112A, the point nearest thereto may be specified, and the NO concentration and the $NH_3$ concentration may be obtained, for example, by a known type of approximation calculation.

Further, the NO concentration and the $NH_3$ concentration may be obtained by the following method. More specifically, as shown in the aforementioned FIG. 5, the relationship between the amount of change ΔIp3 and the $NH_3$ concentration is obtained beforehand by experiment or simulation, and the $NH_3$ concentration is obtained from the amount of change ΔIp3 at a time of turning on and at a time of turning off the preliminary pump cell 80. Then, the NO concentration may be obtained by subtracting the $NH_3$ concentration, which was obtained in the foregoing manner, from the NO concentration obtained from the sensor output at the time that the preliminary pump cell 80 was turned off, or in other words, the total NO concentration obtained by converting the total concentrations of NO and $NH_3$ into NO.

Next, the process of measuring NO and $NH_3$ by the first gas sensor 10A will be described with reference to the flowchart of FIG. 7.

Figure 7:
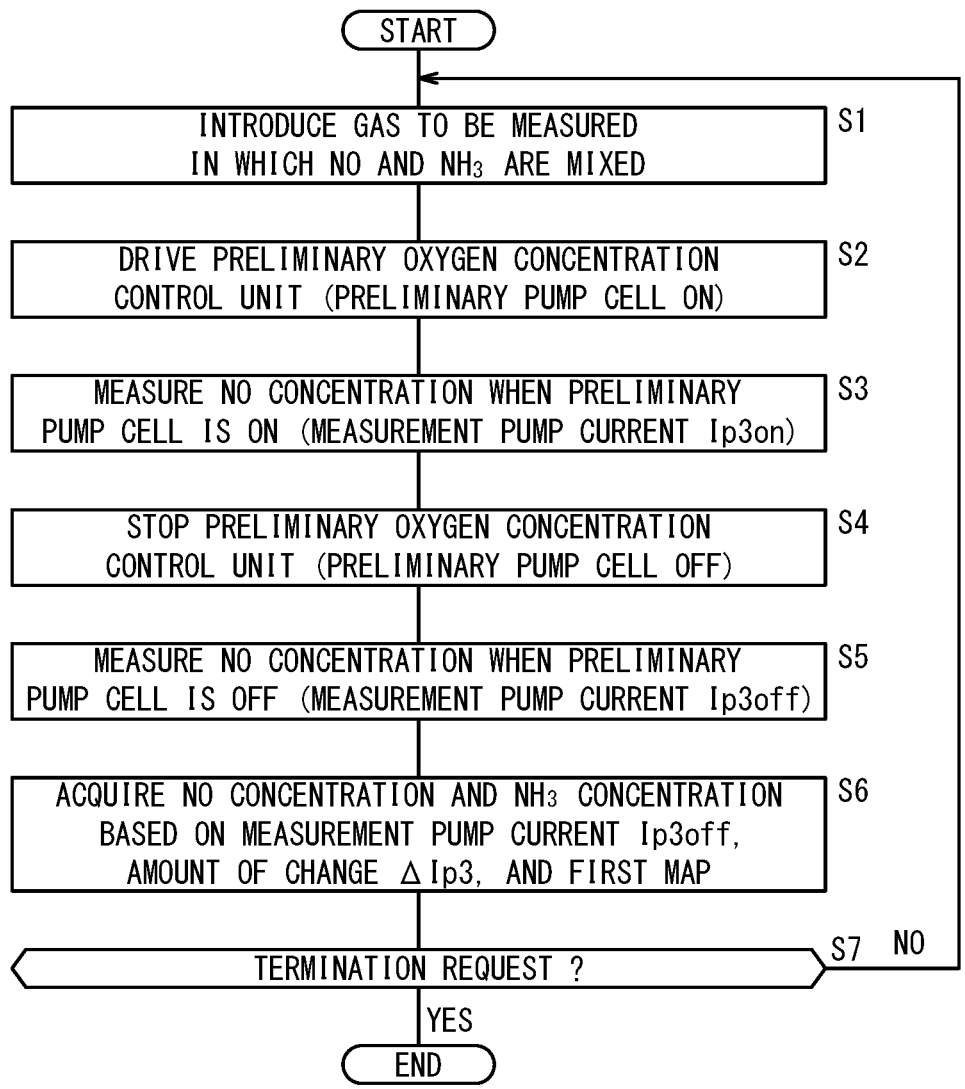
FIG. 7 is a flowchart showing an example of a process of measuring NO and $NH_3$ by the first gas sensor.

First, in step S1 of FIG. 7, the first gas sensor 10A introduces a gas to be measured in which NO and $NH_3$ are mixed into the preliminary adjustment chamber 21 through the gas introduction port 16.

In step S2, the drive control unit 108 drives the preliminary oxygen concentration control unit 106. Consequently, the preliminary pump cell 80 is turned on.

In step S3, the specified component measurement unit 104 measures the NO concentration at the time that the preliminary pump cell 80 is turned on. That is, the measurement pump current Ip3on is acquired. The measurement pump current Ip3on is input to the target component acquisition unit 110.

In step S4, the drive control unit 108 stops driving of the preliminary oxygen concentration control unit 106. Consequently, the preliminary pump cell 80 is turned off.

In step S5, the specified component measurement unit 104 measures the NO concentration at the time that the preliminary pump cell 80 is turned off. That is, the measurement pump current Ip3off is acquired. The measurement pump current Ip3off is input to the target component acquisition unit 110.

In step S6, the target component acquisition unit 110 acquires the NO concentration and the $NH_3$ concentration on the basis of the measurement pump current Ip3off when the preliminary pump cell 80 is turned off, the amount of change ΔIp3 between the measurement pump current Ip3off and the measurement pump current Ip3on when the preliminary pump cell 80 is turned on, and the first map 112A.

More specifically, the target component acquisition unit 110 specifies a point on the first map 112A from the measurement pump current Ip3off and the amount of change ΔIp3. In addition, the NO concentration and the $NH_3$ concentration corresponding to the specified point are read out from the first map 112A, and at this time, the concentrations are set as the measured NO concentration and the measured $NH_3$ concentration. If there is no corresponding point on the first map 112A, as was discussed above, the point nearest thereto is specified, and the NO concentration and the $NH_3$ concentration are obtained, for example, by a known type of approximation calculation.

Alternatively, based on the relationship between the amount of change ΔIp3 and the $NH_3$ concentration shown in FIG. 5, the $NH_3$ concentration is obtained from the amount of change ΔIp3 at a time of turning on and at a time of turning off the preliminary pump cell 80. Then, the NO concentration may be obtained by subtracting the $NH_3$ concentration, which was obtained in the foregoing manner, from the NO concentration obtained from the sensor output at the time that the preliminary pump cell 80 was turned off, or in other words, the total NO concentration obtained by converting the total concentrations of NO and $NH_3$ into NO.

In step S7, the first gas sensor 10A determines whether or not there is a termination request (power off, maintenance, etc.) to terminate the measurement process of NO and $NH_3$. If there is not a termination request, the processes from step S1 and thereafter are repeated. In addition, in step S7, at a stage at which a termination request is made, the process of measuring NO and $NH_3$ in the first gas sensor 10A is brought to an end.

In this manner, the first gas sensor 10A utilizes the first map 112A in which there is recorded a relationship, which is measured experimentally in advance, between the NO concentration and the $NH_3$ concentration respectively for each of points specified by the sensor output (Ip3off) from the specified component measurement unit 104 at a time of stopping the preliminary oxygen concentration control unit 106, and a difference ($\Delta$Ip3) in the sensor outputs from the specified component measurement unit 104 at times of driving and stopping the preliminary oxygen concentration control unit 106. Alternatively, as shown in FIG. 5, a relationship, which was obtained experimentally in advance, between the amount of change $\Delta$Ip3 and the $NH_3$ concentration may be used. Of course, such a feature may also be used in combination with the first map 112A.

In addition, the respective concentrations of NO and $NH_3$ are obtained by comparing with the first map 112A the sensor output (Ip3off) from the specified component measurement unit 104 at the time of stopping the preliminary oxygen concentration control unit 106 during actual use, and the difference ($\Delta$Ip3) in the sensor outputs from the specified component measurement unit 104 at the times of driving and stopping the preliminary oxygen concentration control unit 106.

Consequently, it is possible to accurately measure the respective concentrations of a plurality of target components over a prolonged period, even under an atmosphere of a non-combusted component such as exhaust gas, and a plurality of target components (for example, NO and $NH_3$) that coexist in the presence of oxygen.

In addition, merely by changing the software of the control system of the first gas sensor 10A, the first gas sensor 10A is capable of easily realizing the process of measuring the respective concentrations of NO and $NH_3$ which heretofore could not be realized, without separately adding various measurement devices or the like as hardware. As a result, it is possible to improve the accuracy of controlling an NOx purification system and detecting failures thereof. In particular, it is possible to distinguish between NO and $NH_3$ in exhaust gas downstream of an SCR system, which contributes to precisely controlling the injected amount of urea, as well as detecting deterioration of the SCR system.

Next, a gas sensor (hereinafter referred to as a second gas sensor 10B) according to a second embodiment will be described further with reference to FIGS. 8 to 13.

Figure 8:
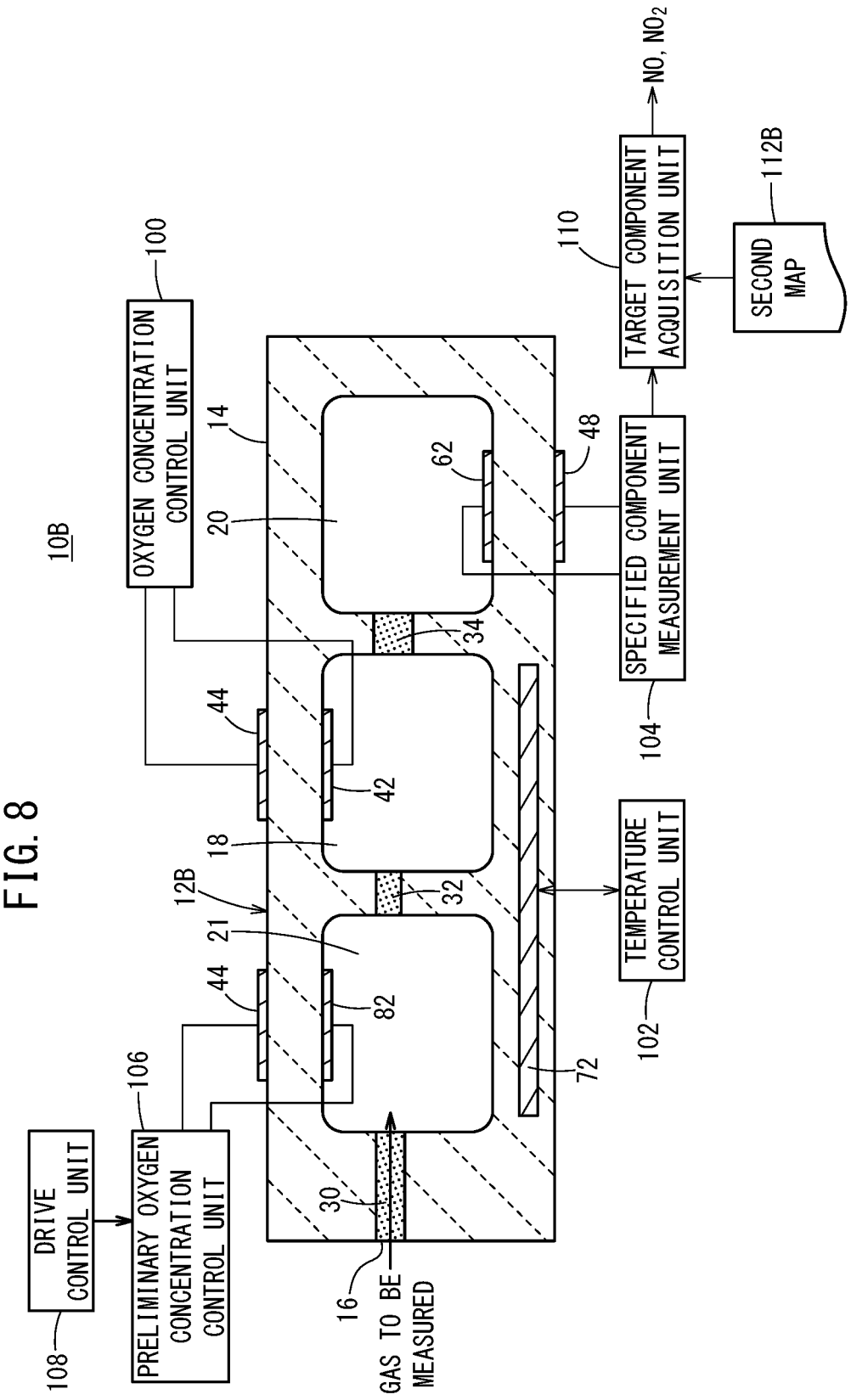
FIG. 8 is a configuration diagram schematically showing a second gas sensor.

As shown in FIG. 8, the second gas sensor 10B is equipped with a second sensor element 12B having the same configuration as that of the first sensor element 12A of the first gas sensor 10A, however, differs therefrom in that the second target component is $NO_2$.

Accordingly, by the oxygen concentration control unit 100 or the temperature control unit 102, or alternatively, by the oxygen concentration control unit 100 and the temperature control unit 102, the second gas sensor 10B performs a control so as to convert all of the $NO_2$ into NO, without causing decomposition of NO inside the oxygen concentration adjustment chamber 18.

On the basis of the preset oxygen concentration condition, and the preliminary electromotive force V0 generated in the preliminary oxygen partial pressure detecting sensor cell 84 (see FIG. 1), the preliminary oxygen concentration control unit 106 feedback-controls the preliminary variable power source 86, thereby adjusting the oxygen concentration inside the preliminary adjustment chamber 21 to a concentration in accordance with the condition.

By the preliminary oxygen concentration control unit 106, all of the $NO_2$ is converted into NO, without causing decomposition of NO inside the preliminary adjustment chamber 21.

The drive control unit 108 controls both driving and stopping of the preliminary oxygen concentration control unit 106. Consequently, the preliminary pump cell 80 is controlled so as to be turned on or off. During driving of the preliminary oxygen concentration control unit 106, the preliminary pump cell 80 is turned on, and therefore, as discussed above, all of the $NO_2$ inside the preliminary adjustment chamber 21 is converted into NO, and flows into the oxygen concentration adjustment chamber 18 through the second diffusion rate control portion 32. While the preliminary oxygen concentration control unit 106 is stopped, the preliminary pump cell 80 is turned off, and therefore, the $NO_2$ inside the preliminary adjustment chamber 21 is not converted into NO, but flows into the oxygen concentration adjustment chamber 18 through the second diffusion rate control portion 32.

The target component acquisition unit 110 acquires the respective concentrations of NO and $NO_2$ on the basis of the sensor output from the specified component measurement unit 104 at the time of driving the preliminary oxygen concentration control unit 106, and the difference in the sensor outputs from the specified component measurement unit 104 at the time of stopping the preliminary oxygen concentration control unit 106.

Next, processing operations of the second gas sensor 10B will be described with reference also to FIGS. 9 and 10.

Figure 9:
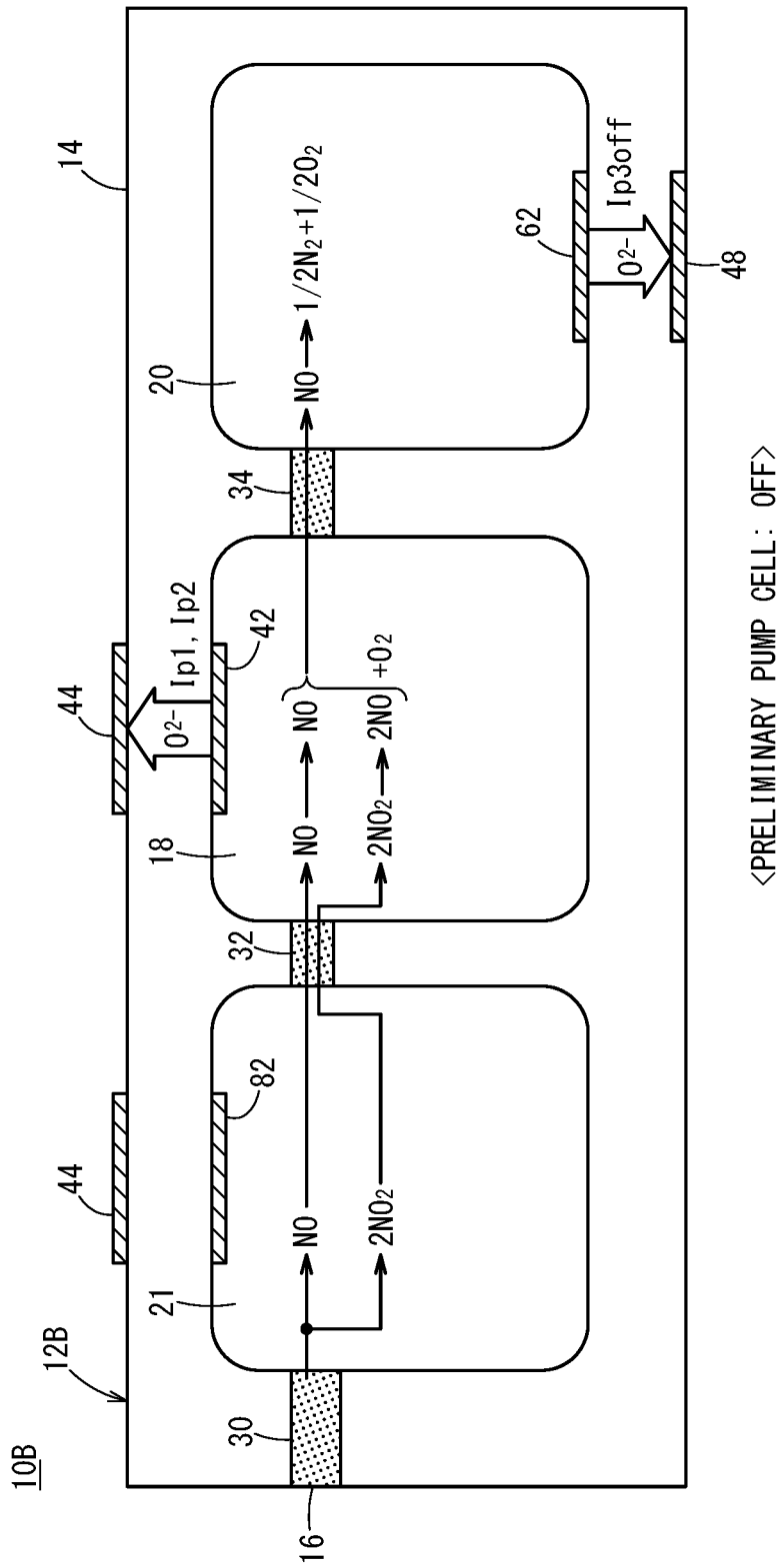
FIG. 9 is an explanatory diagram schematically showing reactions in a preliminary adjustment chamber, an oxygen concentration adjustment chamber, and a measurement chamber, for a case in which a preliminary pump cell is turned off in the second gas sensor.

First, as shown in FIG. 9, the $NO_2$ that was introduced through the gas introduction port 16 reaches the oxygen concentration adjustment chamber 18 during a period in which the preliminary oxygen concentration control unit 106 is stopped by the drive control unit 108. In the oxygen concentration adjustment chamber 18, by operation of the oxygen concentration control unit 100, a control is performed so as to convert all of the $NO_2$ into NO, and therefore, the $NO_2$ that has flowed into the oxygen concentration adjustment chamber 18 from the preliminary adjustment chamber 21 causes a decomposition reaction of $NO_2 \rightarrow NO$ to occur inside the oxygen concentration adjustment chamber 18, and all of the $NO_2$ inside the oxygen concentration adjustment chamber 18 is converted into NO.

Figure 10:
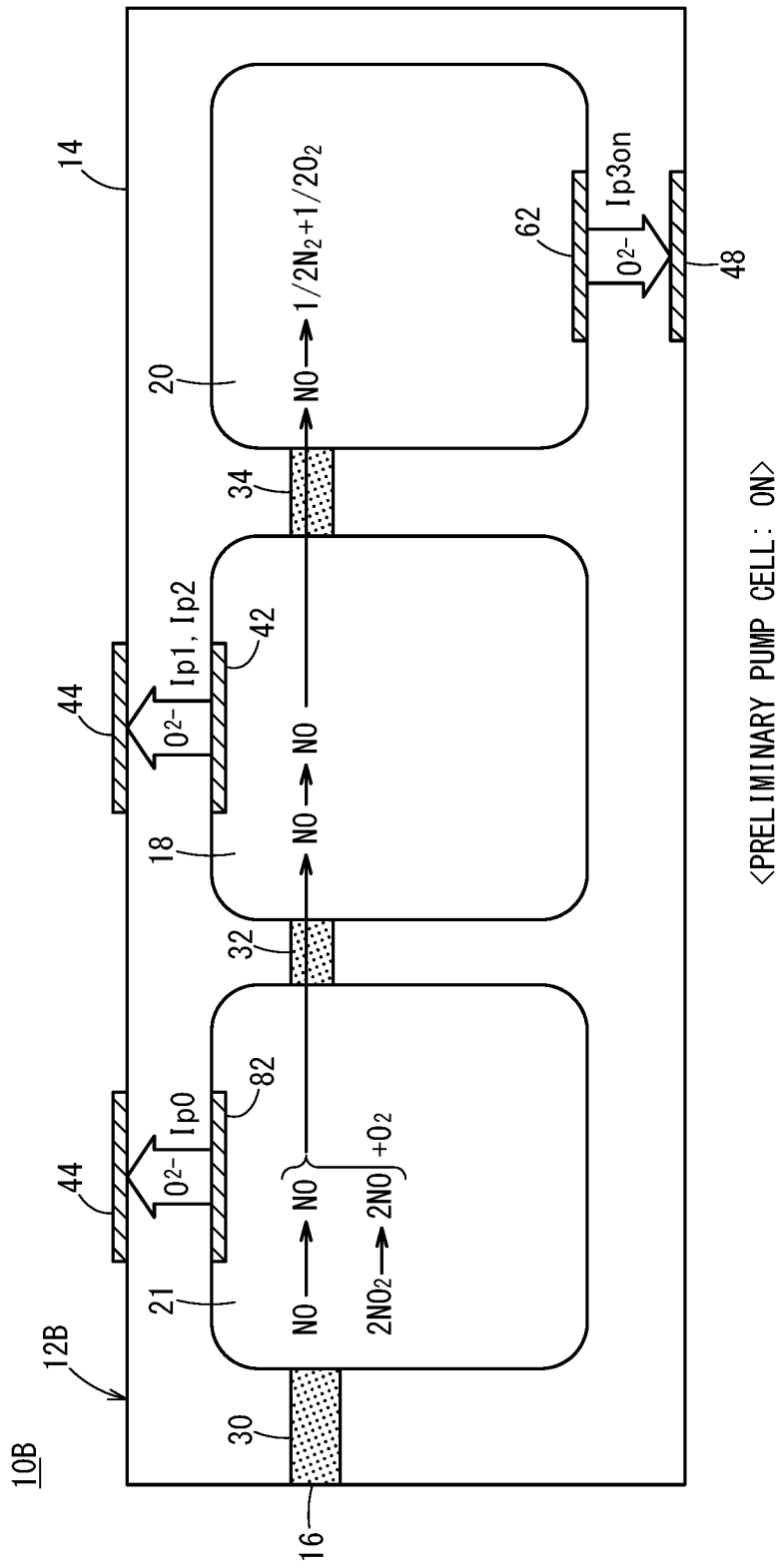
FIG. 10 is an explanatory diagram schematically showing reactions inside the preliminary adjustment chamber, the oxygen concentration adjustment chamber, and the measurement chamber, for a case in which the preliminary pump cell is turned on in the second gas sensor.

On the other hand, during a period in which the preliminary oxygen concentration control unit 106 is being driven by the drive control unit 108, as shown in FIG. 10, the decomposition reaction of $NO_2 \rightarrow NO$ occurs inside the preliminary adjustment chamber 21, and all of the $NO_2$ that was introduced through the gas introduction port 16 is converted into NO.

Stated otherwise, when the preliminary oxygen concentration control unit 106 is switched from a stopped state into a driven state, the location where the decomposition reaction of $NO_2$ takes place is moved from the oxygen concentration adjustment chamber 18 to the preliminary adjustment chamber 21.

The action of moving the location where the decomposition reaction of $NO_2$ takes place from the oxygen concentration adjustment chamber 18 to the preliminary adjustment chamber 21 implies that the state when the $NO_2$ in the gas to be measured passes through the second diffusion rate control portion 32 is equivalent to a state of being changed from $NO_2$ to NO. In addition, since NO and $NO_2$ possess different diffusion coefficients, the difference between passing through the second diffusion rate control portion 32 with NO or passing therethrough with $NO_2$ corresponds to a difference in the amount of NO that flows into the measurement chamber 20, and therefore, the measurement pump current Ip3 that flows to the measurement pump cell 61 is made to change.

In this case, the measurement pump current Ip3on when the preliminary pump cell 80 is turned on, and the amount of change ΔIp3 in the measurement pump current Ip3off when the preliminary pump cell 80 is turned off are uniquely determined by the concentration of $NO_2$ in the gas to be measured. Therefore, it is possible to calculate the concentrations of NO and $NO_2$ from the measurement pump current Ip3on or Ip3off when the preliminary pump cell 80 is turned on or off, and the amount of change ΔIp3 in the aforementioned measurement pump current Ip3.

Accordingly, in the target component acquisition unit 110, the respective concentrations of NO and $NO_2$ are acquired on the basis of the measurement pump current Ip3off when the preliminary pump cell 80 is turned off, the amount of change ΔIp3 between the measurement pump current Ip3off and the measurement pump current Ip3on when the preliminary pump cell 80 is turned on, and the second map 112B (see FIG. 8).

Figure 11:
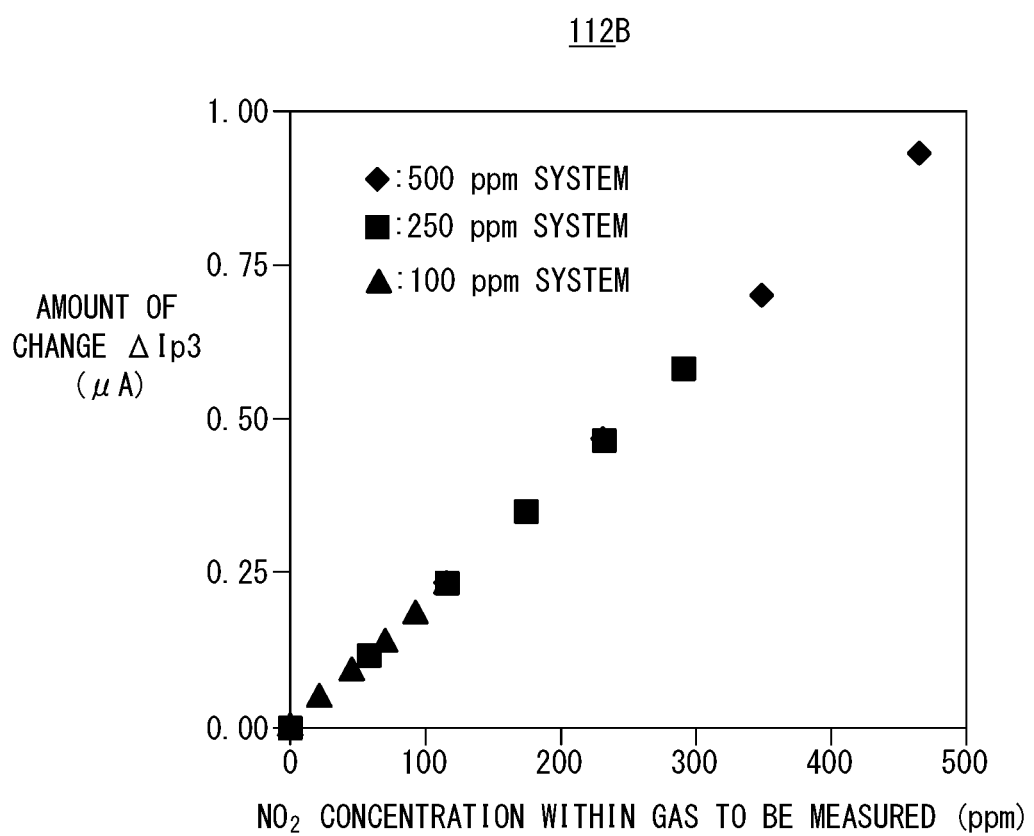
FIG. 11 is a view graphically showing a second map utilized by the second gas sensor.

When shown in the form of a graph, the second map 112B becomes a graph in which, as shown in FIG. 11, the $NO_2$ concentration (ppm) within the gas to be measured is set on the horizontal axis, and there is set on the vertical axis the difference, or in other words, the amount of change ΔIp3 between the measurement pump current Ip3on at a time that the preliminary pump cell 80 is turned on, and the measurement pump current Ip3off at a time that the preliminary pump cell 80 is turned off. In FIG. 11, there is shown representatively a graph in which the NO concentration converted values of the measurement pump current values, at the time that the preliminary pump cell 80 is turned off, are plotted as points pertaining to, for example, a 500 ppm system, a 250 ppm system, and a 100 ppm system. When shown in the form of a table to facilitate understanding, the contents thereof are as shown in FIG. 12. These concentrations are obtained by experiment or simulation.

As can be understood from FIG. 12, by using the second map 112B, and on the basis of the measurement pump current Ip3off when the preliminary pump cell 80 is turned off (i.e., a measurement pump current value similar to that of a conventional serial two-chamber type NOx sensor), any one of the 500 ppm system, the 250 ppm system, and the 100 ppm system is determined and used to identify the respective concentrations of NO and $NO_2$ based on the amount of change ΔIp3.

More specifically, by specifying a point on the second map 112B from the measurement pump current Ip3off when the preliminary pump cell 80 is turned off, and the amount of change ΔIp3, it is possible to identify the NO concentration and the $NO_2$ concentration. For example, in the case that the measurement pump current Ip3off, which is similar to that of a conventional serial two-chamber type NOx sensor, is 10.67 μA, using the aforementioned serial two-chamber type NOx sensor, could only be understood that the total concentrations of NO and $NO_2$ is approximately 500 ppm. However, in the second gas sensor 10B, by being combined with the amount of change ΔIp3, it is possible to individually specify the NO concentration and the $NO_2$ concentration, in a manner so that the NO concentration is 500 ppm and the $NO_2$ concentration is 0 ppm at point p101, the NO concentration is 400 ppm and the $NO_2$ concentration is 116 ppm at point p102, and the NO concentration is 300 ppm and the $NO_2$ concentration is 233 ppm at point p103. If there is no corresponding point on the second map 112B, the point nearest thereto may be specified, and the NO concentration and the $NO_2$ concentration may be obtained, for example, by a known type of approximation calculation.

Further, the NO concentration and the $NO_2$ concentration may be obtained by the following method. More specifically, as shown in the aforementioned FIG. 11, the relationship between the amount of change ΔIp3 and the $NO_2$ concentration is obtained beforehand by experiment or simulation, and the $NO_2$ concentration is obtained from the amount of change ΔIp3 at a time of turning on and at a time of turning off the preliminary pump cell 80. Then, the NO concentration may be obtained by subtracting the $NO_2$ concentration, which was obtained in the foregoing manner, from the NO concentration obtained from the sensor output at the time that the preliminary pump cell 80 was turned off, or in other words, the total NO concentration obtained by converting the total concentrations of NO and $NO_2$ into NO.

Next, the process of measuring NO and $NO_2$ by the second gas sensor 10B will be described with reference to the flowchart of FIG. 13.

Figure 13:
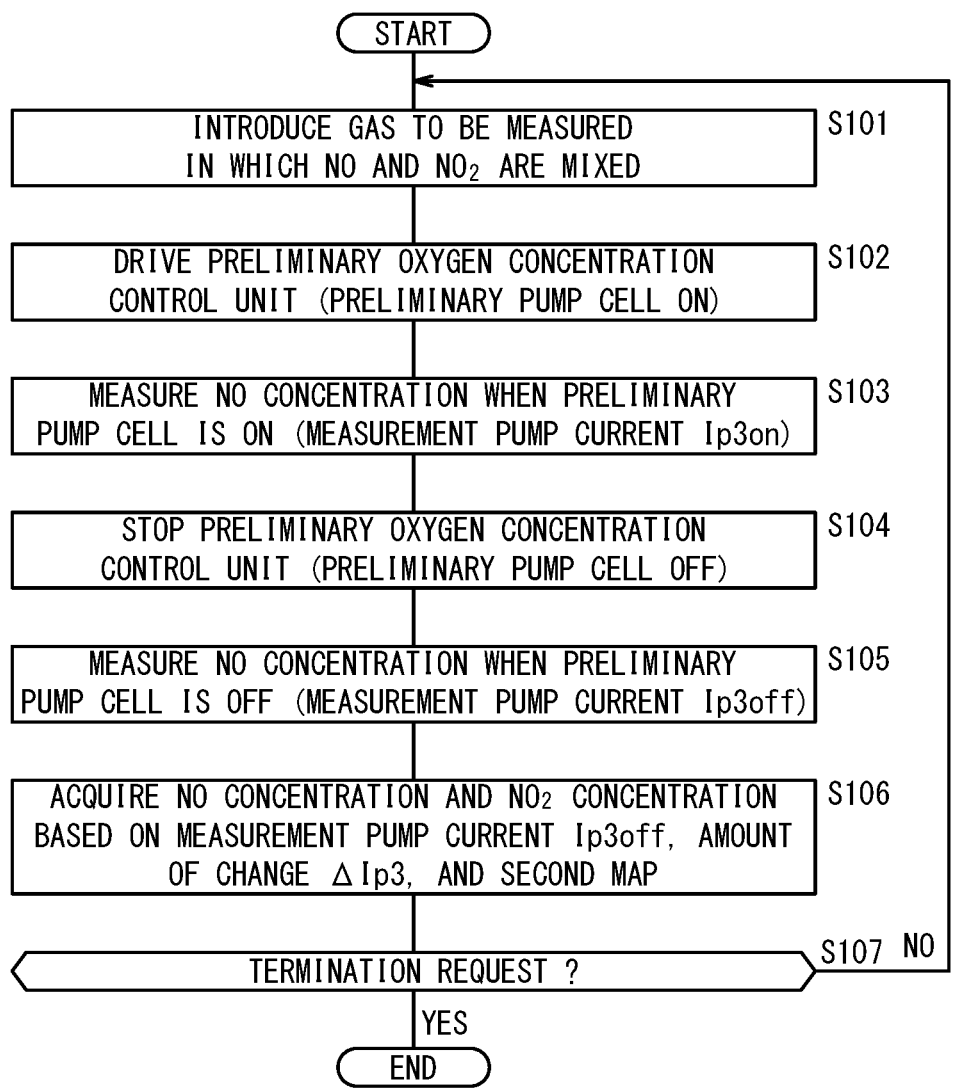
FIG. 13 is a flowchart showing an example of a process of measuring NO and $NO_2$ by the second gas sensor.

First, in step S101 of FIG. 13, the second gas sensor 10B introduces a gas to be measured in which NO and $NO_2$ are mixed into the preliminary adjustment chamber 21 through the gas introduction port 16.

In step S102, the drive control unit 108 drives the preliminary oxygen concentration control unit 106. Consequently, the preliminary pump cell 80 is turned on.

In step S103, the specified component measurement unit 104 measures the NO concentration at the time that the preliminary pump cell 80 is turned on. That is, the measurement pump current Ip3on is acquired. The measurement pump current Ip3on is input to the target component acquisition unit 110.

In step S104, the drive control unit 108 stops driving of the preliminary oxygen concentration control unit 106. Consequently, the preliminary pump cell 80 is turned off.

In step S105, the specified component measurement unit 104 measures the NO concentration at the time that the preliminary pump cell 80 is turned off. That is, the measurement pump current Ip3off is acquired. The measurement pump current Ip3off is input to the target component acquisition unit 110.

In step S106, the target component acquisition unit 110 acquires the NO concentration and the $NO_2$ concentration on the basis of the measurement pump current Ip3off when the preliminary pump cell 80 is turned off, the amount of change ΔIp3 between the measurement pump current Ip3off and the measurement pump current Ip3on when the preliminary pump cell 80 is turned on, and the second map 112B.

More specifically, the target component acquisition unit 110 specifies a point on the second map 112B from the measurement pump current Ip3off and the amount of change ΔIp3. In addition, the NO concentration and the $NO_2$ concentration corresponding to the specified point are read out from the second map 112B, and at this time, the concentrations are set as the measured NO concentration and the measured $NO_2$ concentration. If there is no corresponding point on the second map 112B, in the manner described above, the point nearest thereto is specified, and the NO concentration and the $NO_2$ concentration are obtained, for example, by a known type of approximation calculation.

Alternatively, based on the relationship between the amount of change ΔIp3 and the $NO_2$ concentration shown in FIG. 11, the $NO_2$ concentration is obtained from the amount of change ΔIp3 at a time of turning on and at a time of turning off the preliminary pump cell 80. Then, the NO concentration may be obtained by subtracting the $NO_2$ concentration, which was obtained in the foregoing manner, from the NO concentration obtained from the sensor output at the time that the preliminary pump cell 80 was turned off, or in other words, the total NO concentration obtained by converting the total concentrations of NO and $NO_2$ into NO.

In step S107, the second gas sensor 10B determines whether or not there is a termination request (power off, maintenance, etc.) to terminate the measurement process of NO and $NO_2$. If there is not a termination request, the processes from step S101 and thereafter are repeated. In addition, in step S107, at a stage at which a termination request is made, the process of measuring NO and $NO_2$ in the second gas sensor 10B is brought to an end.

In this manner, the second gas sensor 10B utilizes the second map 112B in which there is recorded a relationship, which is measured experimentally in advance, between the NO concentration and the $NO_2$ concentration respectively for each of points specified by the sensor output (Ip3off) from the specified component measurement unit 104 at a time of stopping the preliminary oxygen concentration control unit 106, and a difference ($\Delta$Ip3) in the sensor outputs from the specified component measurement unit 104 at times of driving and stopping the preliminary oxygen concentration control unit 106. Alternatively, as shown in FIG. 11, a relationship, which was obtained experimentally in advance, between the amount of change $\Delta$Ip3 and the $NO_2$ concentration may be used. Of course, such a feature may also be used in combination with the second map 112B.

In addition, the respective concentrations of NO and $NO_2$ are obtained by comparing with the second map 112B the sensor output (Ip3off) from the specified component measurement unit 104 at the time of stopping the preliminary oxygen concentration control unit 106 during actual use, and the difference ($\Delta$Ip3) in the sensor outputs from the specified component measurement unit 104 at the times of driving and stopping the preliminary oxygen concentration control unit 106.

Consequently, it is possible to accurately measure the respective concentrations of a plurality of target components over a prolonged period, even under an atmosphere of a non-combusted component such as exhaust gas, and a plurality of target components (for example, NO and $NO_2$) that coexist in the presence of oxygen.

In addition, merely by changing the software of the control system of the second gas sensor 10B, the second gas sensor 10B is capable of easily realizing the process of measuring the respective concentrations of NO and $NO_2$ which heretofore could not be realized, without separately adding various measurement devices or the like as hardware. As a result, it is possible to improve the accuracy of controlling an NOx purification system and detecting failures thereof. In particular, it is possible to distinguish between NO and $NO_2$ in exhaust gas downstream of a DOC catalyst (Diesel Oxidation Catalyst), which contributes to detecting deterioration of the DOC catalyst.

The essence and gist of the present invention is characterized by the following items (a) to (c), and the reaction by which $NH_3$ or $NO_2$ is changed into NO can be arbitrarily selected from within a range in which a variation in the sensor outputs can be obtained.

(a) A reaction is intentionally generated in which $NH_3$ or $NO_2$ changes into NO before and after a diffusion rate control portion possessing a predetermined diffusion resistance.

(b) According to item (a), the concentration of $NH_3$ or $NO_2$ is determined from a variation in the sensor outputs caused by a difference between the diffusion coefficients of NO and $NH_3$, or the diffusion coefficients of NO and $NO_2$.

(c) Furthermore, the NO concentration is obtained by comparing the total concentrations of NO and $NH_3$ or the total concentrations of NO and $NO_2$ obtained by the sensor output itself with the concentration of $NH_3$ or $NO_2$ obtained due to the variation.

Next, an exhaust gas purification system 200 which includes the first gas sensor 10A and the second gas sensor 10B will be described with reference to FIGS. 14 to 19.

Figure 14:
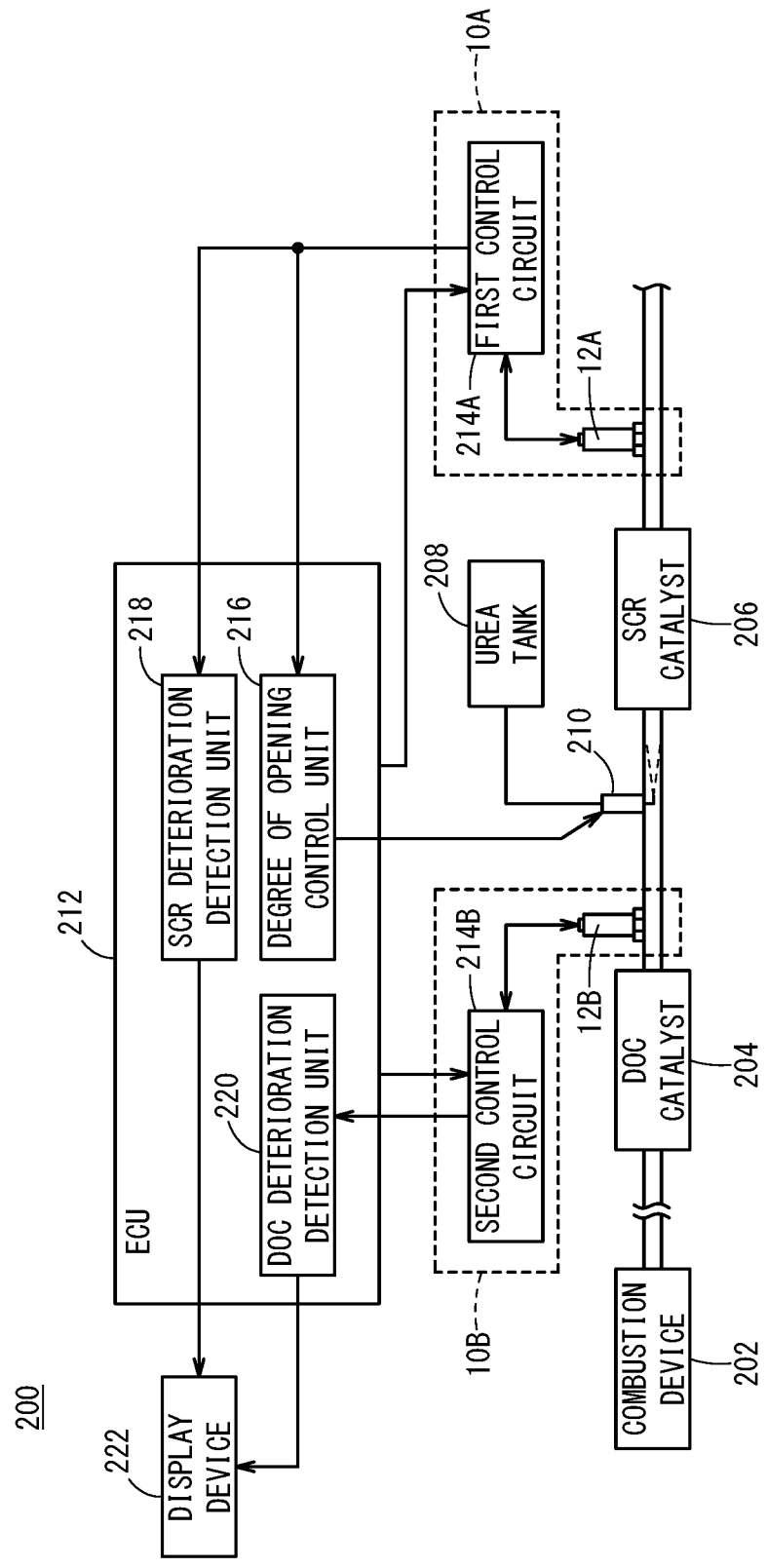
FIG. 14 is a configuration diagram showing an exhaust gas purification system according to the present embodiment.

As shown in FIG. 14, the exhaust gas purification system 200 is a system for purifying exhaust gas from a combustion device 202 such as a diesel engine or the like. The exhaust gas purification system 200 includes a DOC catalyst 204 which serves to reduce hydrocarbons and carbon oxides from the combustion device 202, an SCR catalyst 206 installed on a downstream side of the DOC catalyst 204, and a urea water injector 210 that injects urea water, which is stored in a urea tank 208, onto the SCR catalyst 206 from an upstream side thereof. The concept of injection also encompasses injection by way of spraying. The combustion device 202 applies energy to a load (such as a crankshaft) based on a predetermined combustion control performed by an ECU 212 (electronic control unit), for example.

In addition, the first sensor element 12A of the first gas sensor 10A is disposed downstream of the SCR catalyst 206, and the second sensor element 12B of the second gas sensor 10B is disposed between the DOC catalyst 204 and the SCR catalyst 206, and more specifically, is installed between the DOC catalyst 204 and the urea water injector 210.

A first control circuit 214A which controls driving of the first gas sensor 10A is connected between the ECU 212 and the first sensor element 12A, and a second control circuit 214B which controls driving of the second gas sensor 10B is connected between the ECU 212 and the second sensor element 12B.

The first control circuit 214A controls the above-described oxygen concentration control unit 100 which is specialized for the first gas sensor 10A, the temperature control unit 102, the specified component measurement unit 104, the preliminary oxygen concentration control unit 106, the drive control unit 108, and the target component acquisition unit 110, etc.

Similarly, the second control circuit 214B controls the above-described oxygen concentration control unit 100 which is specialized for the second gas sensor 10B, the temperature control unit 102, the specified component measurement unit 104, the preliminary oxygen concentration control unit 106, the drive control unit 108, and the target component acquisition unit 110, etc.

Further, inside the ECU 212, there are included a degree of opening control unit 216 that controls the degree of opening of the urea water injector 210 on the basis of the NO concentration and the $NH_3$ concentration from the first control circuit 214A, an SCR deterioration detection unit 218 that detects a state of degradation of the SCR catalyst 206 based on the NO concentration and the $NH_3$ concentration, and a DOC deterioration detection unit 220 that detects a state of degradation of the DOC catalyst 204 based on the NO concentration and the $NO_2$ concentration from the second control circuit 214B.

Moreover, concerning the ECU 212 as well, it is constituted by one or more electronic circuits having, for example, one or a plurality of CPUs (central processing units), memory devices, and the like. The above-described degree of opening control unit 216, the SCR deterioration detection unit 218, and the DOC deterioration detection unit 220 are also software-based functional units in which predetermined functions are realized, for example, by the CPUs executing programs stored in a storage device. Of course, the electronic circuits may be constituted by an integrated circuit such as an FPGA, in which the plurality of electronic circuits are connected according to the functions thereof.

First, for the sake of comparison, a change in the NO concentration, a change in the $NH_3$ emission level, and a change in the SCR efficiency, which are measured with a conventional gas sensor in the case that the injected amount of urea water is increased will be explained with reference to FIG. 15.

Figure 15:
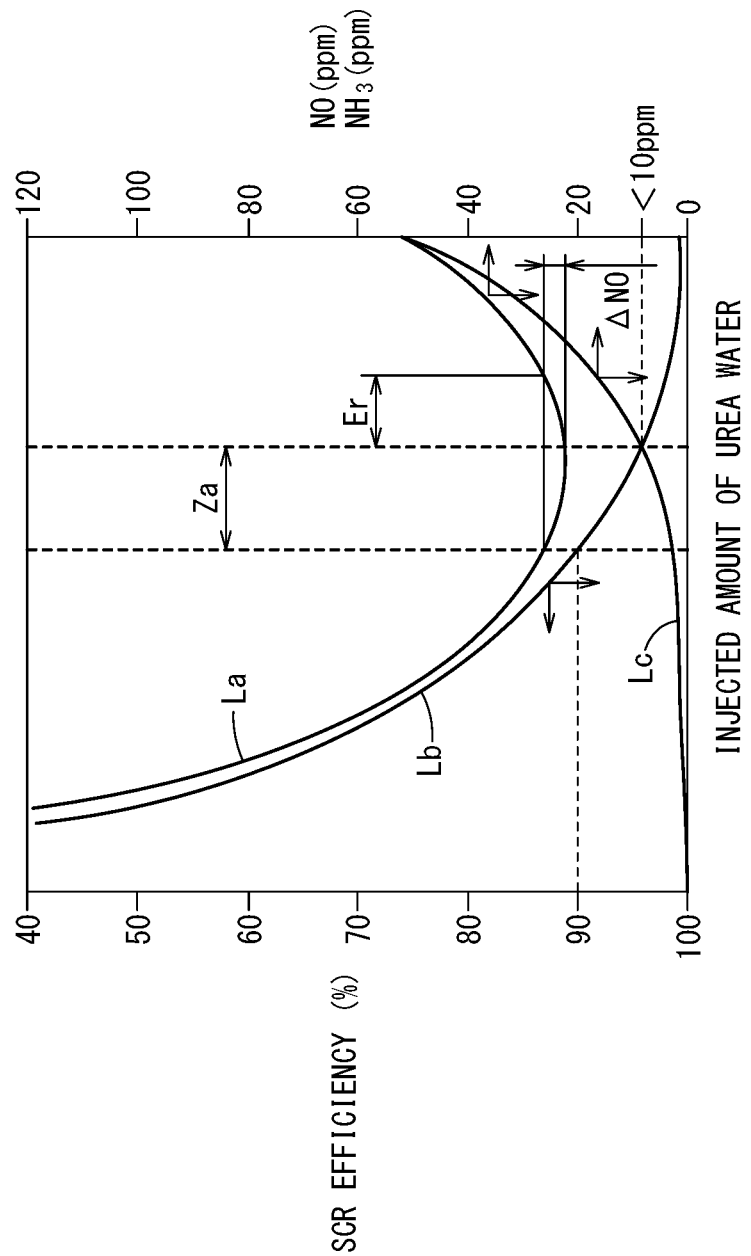
FIG. 15 is a graph showing an SCR efficiency (%), an emission level of $NH_3$ (ppm), and an NO concentration (ppm) measured by a conventional gas sensor with respect to changes in an injected amount of urea water.

In FIG. 15, on the left vertical axis, there is shown the SCR efficiency (the NOx purification efficiency (%) of the SCR catalyst 206), on the right vertical axis, there is shown the $NH_3$ emission level (ppm) and the NO concentration (ppm) as measured by a conventional gas sensor, and on the horizontal axis, there is shown the injected amount of urea water. In FIG. 15, the characteristic curve La indicates the NO concentration, the characteristic curve Lb indicates the SCR efficiency, and the characteristic curve Lc indicates the $NH_3$ emission level.

As can be understood from FIG. 15, by causing an increase in the injected amount of urea water, although the SCR efficiency increases, the amount of $NH_3$ that is discharged also increases. Therefore, as a target detection range Za by the gas sensor, it is preferable to set a lower limit of the SCR efficiency to 90%, and to set an upper limit of the $NH_3$ emission level to 10 ppm.

However, due to the influence of interference caused by an increase in the $NH_3$ emission level, the sensitivity of the gas sensor (the variation width $\Delta NO$ of the measurement value of the gas sensor with respect to an incremental width of the urea water injection amount) becomes small in a region in which the SCR efficiency is greater than or equal to 90%, while additionally, since an error component Er is also included therein, a problem results in that a precise control of the injected amount of urea water cannot be assured.

Figure 16:
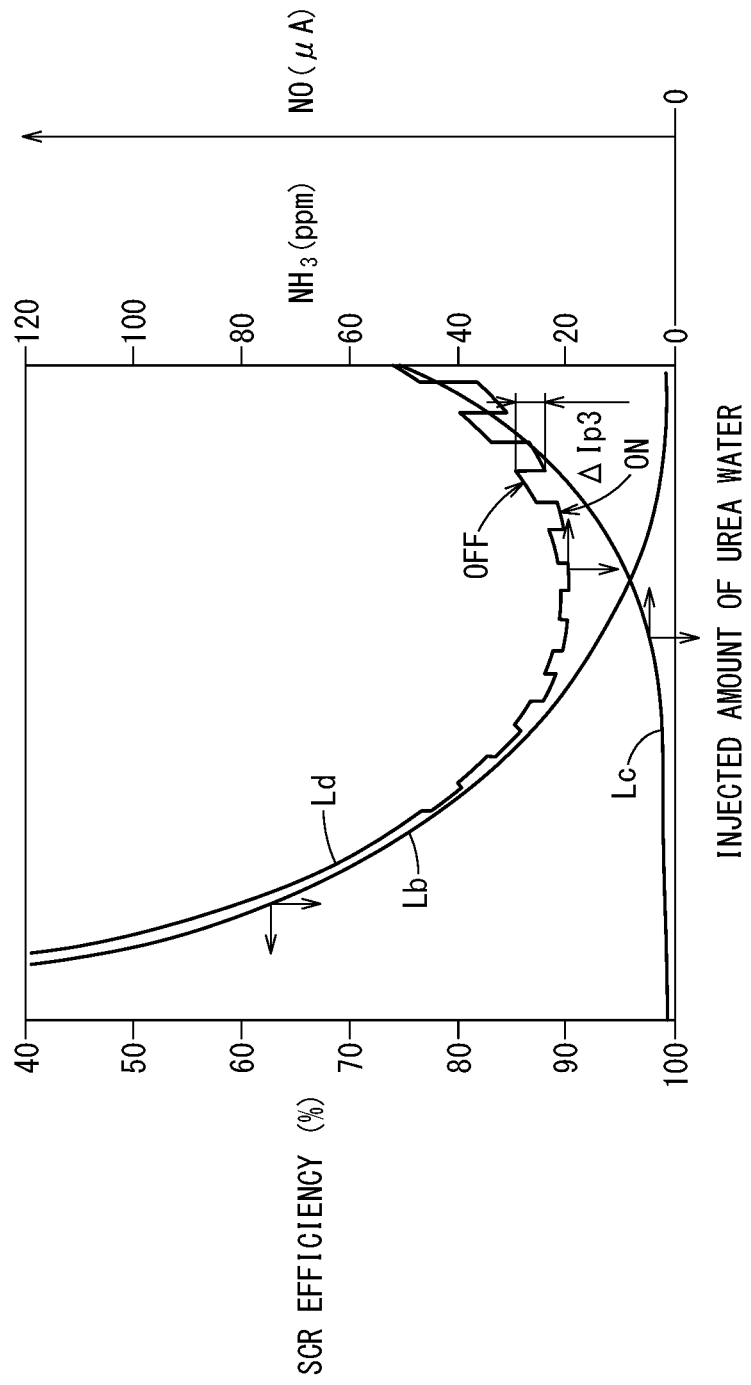
FIG. 16 is a graph showing an SCR efficiency (%), an emission level of $NH_3$ (ppm), and a sensor output (NO output (μA)) of the first gas sensor with respect to changes in an injected amount of urea water.

On the other hand, FIG. 16 shows a change in the sensor output of the first gas sensor 10A, a change in the $NH_3$ emission level, and a change in the SCR efficiency, in the case that the injected amount of urea water is increased. In FIG. 16, the SCR efficiency (%) is shown on the left vertical axis, the $NH_3$ emission level (ppm) and the sensor output Ip3 ($\mu A$) of the first gas sensor 10A are shown on the right vertical axis, and the injected amount of urea water is shown on the horizontal axis. In FIG. 16, the characteristic curve Ld indicates the sensor output, the characteristic curve Lb indicates the SCR efficiency, and the characteristic curve Lc indicates the $NH_3$ emission level.

In the first gas sensor 10A, the sensor output Ip3 from the specified component measurement unit 104 undergoes variations corresponding to driving and stopping of the preliminary oxygen concentration control unit 106, and more specifically, responsive to the preliminary pump cell 80 being turned on and off. The variation ($\Delta Ip3$) in the sensor output Ip3 increases as the concentration of $NH_3$ increases. Accordingly, as described above, the respective concentrations of NO and $NH_3$ are acquired on the basis of the measurement pump current Ip3on when the preliminary pump cell 80 is turned on, the amount of change $\Delta Ip3$ between the measurement pump current Ip3on and the measurement pump current Ip3off when the preliminary pump cell 80 is turned off, and the first map 112A.

Conventionally, the concentrations of NO and $NH_3$ have been measured using only the sensor output when $NH_3$ is subjected to an oxidation reaction and is converted into NO, without causing decomposition of NO in the oxygen concentration adjustment chamber 18. In contrast thereto, in the first gas sensor 10A, in addition to the sensor output Ip3off obtained when $NH_3$ is directly introduced into the oxygen concentration adjustment chamber 18 without the $NH_3$ being subjected to an oxidation reaction, and without causing decomposition of NO in the preliminary adjustment chamber 21, the NO concentration and the $NH_3$ concentration are acquired from the first map 112A on the basis of the amount of change $\Delta Ip3$. The amount of change $\Delta Ip3$ is indicative of an amount of change between the sensor output Ip3off and the sensor output Ip3on when the $NH_3$ is subjected to the oxidation reaction without causing decomposition of NO in the preliminary adjustment chamber 21.

Therefore, the concentration corresponding to the sensor output of the first gas sensor 10A can be divided into an $NH_3$ concentration (a concentration corresponding to the amount of change $\Delta Ip3$), and an NO concentration (a concentration corresponding to the concentration and the amount of change $\Delta Ip3$ corresponding to the sensor output of the first gas sensor 10A).

Therefore, as for the target detection range Za by the first gas sensor 10A, as described above, the lower limit of the SCR efficiency is set to 90%, and the upper limit of the $NH_3$ discharge amount is set to 10 ppm, and for example, even if the variation width of the sensor output Ip3off is small, it is possible to accurately acquire the NO concentration and the $NH_3$ concentration.

As a result, assuming that the injected amount of urea water is adjusted in a manner so that the $NH_3$ concentration and the NO concentration are respectively less than or equal to predetermined individual concentrations, the NOx purification system can be accurately controlled.

Next, the relationship between the injected amount of urea water and the sensor output of the first gas sensor 10A will be described with reference to FIGS. 17A and 17B.

Figure 17B:
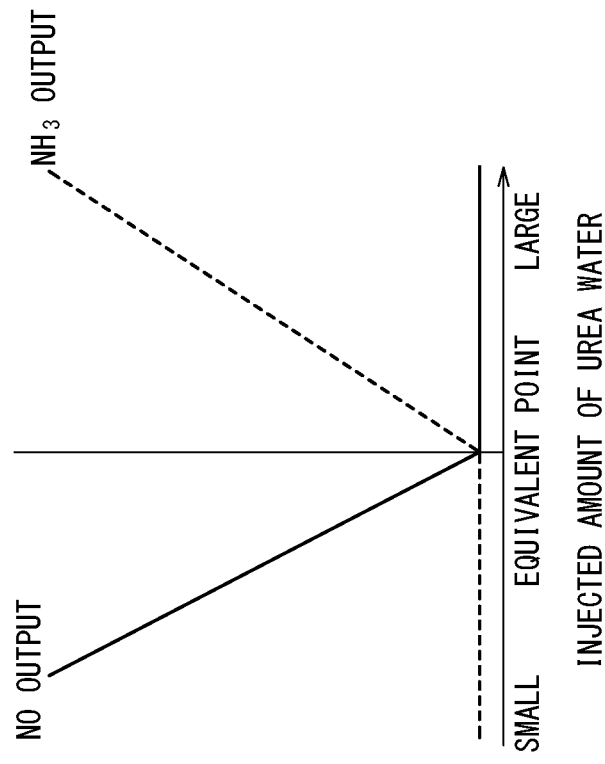
FIG. 17B is a graph separated into a sensor output (NO output) in regards to NO, and a sensor output ($NH_3$ output) in regards to $NH_3$.
Figure 17A:
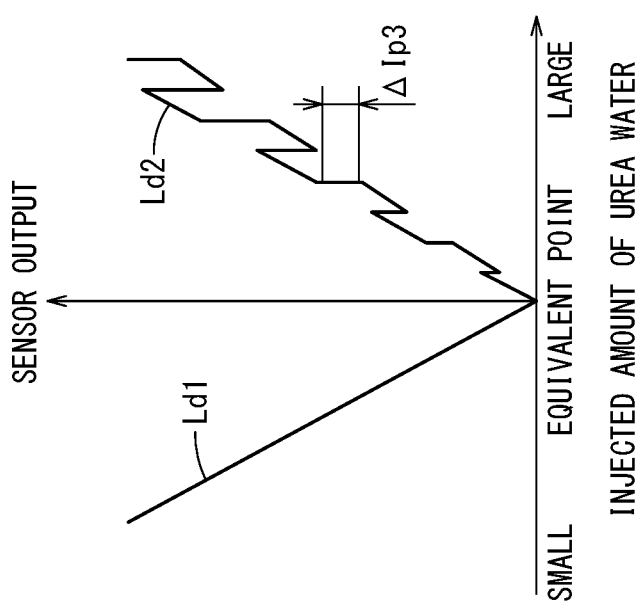
FIG. 17A is a graph showing a relationship between an injected amount of urea water and the sensor output of the first gas sensor.

FIG. 17A shows a relationship between an excess or deficiency in the injected amount of urea water and the sensor output of the first gas sensor 10A. In the region where the injected amount of urea water is less than an equivalent point, since all of the $NH_3$ produced by the injection of urea water is consumed by the decomposition of NOx, there is almost no outflow of $NH_3$. Therefore, the sensor output of the first gas sensor 10A is substantially the same as the sensor output when the preliminary pump cell 80 is turned on and the sensor output when the preliminary pump cell 80 is turned off, and as indicated by the solid line Ld1 in FIG. 17A, decreases linearly as the injected amount of urea water increases. In addition, the sensor output becomes lowest at the equivalent point.

On the other hand, when the injected amount of urea water exceeds the equivalent point, since an excessive amount of urea remains in the form of $NH_3$, the residual $NH_3$ emission level is detected as the amount of change $\Delta Ip3$ between the sensor output when the preliminary pump cell 80 is turned on and the sensor output when the preliminary pump cell 80 is turned off. More specifically, as indicated by the solid line Ld2 in FIG. 17A, the sensor output of the first gas sensor 10A exhibits a rectangular shape. In addition, the amount of change $\Delta Ip3$ increases accompanying an increase in the outflow amount of $NH_3$.

The sensor output of the first gas sensor 10A, which is shown in FIG. 17A, can be separated into a sensor output (NO output) in regards to NO, and a sensor output ($NH_3$ output) in regards to $NH_3$, as shown in FIG. 17B. In this case, the NO output decreases linearly toward the equivalent point in the region where the injected amount of urea water is deficient. In addition, the NO output becomes a lowest value at the equivalent point of the urea water inflow amount, and is maintained at the lowest value in the region where the injected amount of urea water is excessive.

In a contrary manner to the NO output, the $NH_3$ output exhibits a lowest value at the equivalent point and in the region where the injected amount of urea water is deficient, and in a region where the injected amount of urea water is excessive, exhibits an output corresponding to the concentration of $NH_3$ generated by the excess urea.

By controlling the degree of opening of the urea water injector 210 (hereinafter referred to as the degree of opening of the urea injector) utilizing the change in the NO output and the $NH_3$ output with respect to the injected amount of urea water, it is possible to control the exhaust gas purification system 200 under a condition in which the NOx purification efficiency is higher.

As an example, a description will be given with reference to FIGS. 18A to 18C concerning the control of the degree of opening of the urea injector using changes in NO output (NO concentration) and $NH_3$ output ($NH_3$ concentration). FIG. 18A is a graph showing changes in the NO output accompanying an elapse of time, FIG. 18B is a graph showing changes in the $NH_3$ output accompanying an elapse of time, and FIG. 18C is a graph showing changes in the degree of opening of the urea injector accompanying an elapse of time.

First, the degree of opening of the urea injector undergoes expansion from time t0 when the NO output (NO concentration) has reached a first threshold value Th1. The first threshold value Th1 is set to a value that is higher than the NO output at the respective equivalent points of the NO output and the $NH_3$ output.

The NO output decreases until time t1 when the injected amount of urea water reaches the equivalent point, and the NO output is maintained at the minimum value even after having passed through the equivalent point.

The $NH_3$ output ($NH_3$ concentration) starts to increase from time t1 upon having passed through the equivalent point, and therefore, the degree of opening of the urea injector starts to be restricted at time t2 when the $NH_3$ output reaches a second threshold value Th2. The second threshold value Th2 is set to a value that is higher than the $NH_3$ output at the respective equivalent points of the NO output and the $NH_3$ output. For example, it is set to a value at which the $NH_3$ output corresponds to 2 to 10 ppm.

When the degree of opening of the urea injector is continuously throttled, the $NH_3$ output begins to decrease, the $NH_3$ output reaches a minimum value at time t3 upon having reached the equivalent point, and is maintained at the minimum value even after having passed through the equivalent point.

The NO output starts to increase from time t3 upon having passed through the equivalent point, and thereafter reaches the first threshold value Th1 at time t4. Hence, the degree of opening of the urea injector starts to be expanded at time t4. Thereafter, since the control operations are the same as those after time t0, explanation of such operations will be omitted.

As described above, in the first gas sensor 10A, it is possible to distinguish between NO and $NH_3$ in exhaust gas downstream of the SCR catalyst 206. In this case, it is effective to measure an NO/$NH_3$ ratio in order to detect deterioration of the SCR catalyst 206. Accordingly, as shown in FIG. 14, in the SCR deterioration detection unit 218 inside the ECU 212, the NO/$NH_3$ ratio is calculated based on the NO concentration and the $NH_3$ concentration from the first control circuit 214A, whereby it is possible to detect the deterioration of the SCR catalyst 206. Information concerning the deterioration of the SCR catalyst 206 is displayed, for example, through a display device 222. Further, even if $NO_2$ is present in the exhaust gas downstream of the SCR catalyst 206, by using a correction value obtained experimentally or an empirical correction value, it is possible to control the SCR catalyst system so as to be substantially free of problems.

Similarly, in the second gas sensor 10B, it is possible to distinguish between NO and $NO_2$ in exhaust gas downstream of the DOC catalyst 204. In this case, upon initial degradation (a reduction in oxidizing capacity) of the DOC catalyst 204, a change in the NO/$NO_2$ ratio (reduction in $NO_2$) is more conspicuous than an increase in the emitted amount of non-combusted components such as HC or the like. Accordingly, in the DOC deterioration detection unit 220 inside the ECU 212, the NO/$NO_2$ ratio is calculated based on the NO concentration and the $NO_2$ concentration from the second control circuit 214B, whereby it is possible to detect the deterioration of the DOC catalyst 204. Information concerning the deterioration of the DOC catalyst 204 is displayed, for example, through the display device 222.

Figure 19:
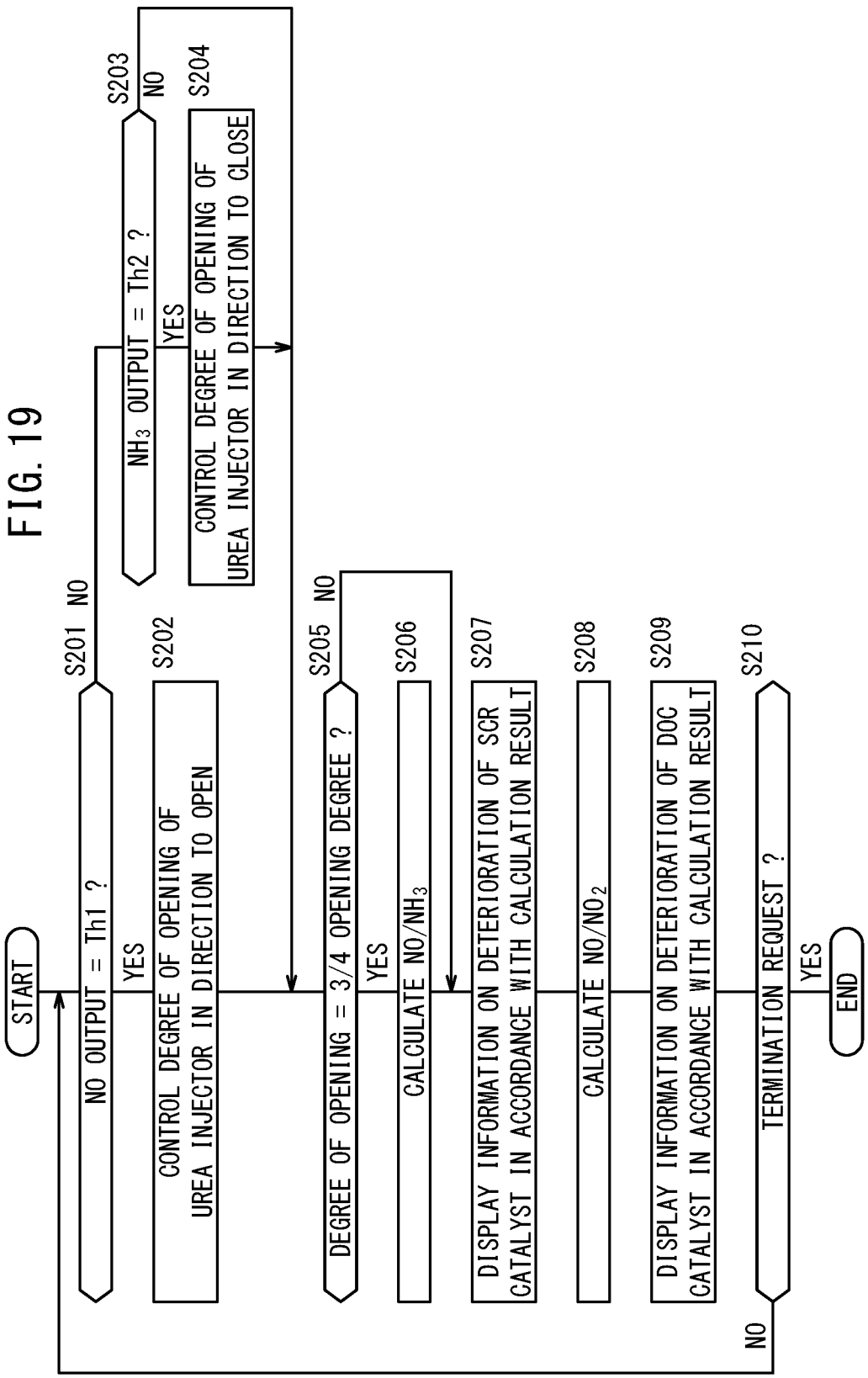
FIG. 19 is a flowchart showing an example of a processing operation of the exhaust gas purification system according to the present embodiment.

Next, processing operations of the exhaust gas purification system 200 according to the present embodiment will be described with reference to the flowchart of FIG. 19.

First, in step S201, the degree of opening control unit 216 determines whether or not the NO output (NO concentration) from the first control circuit 214A has reached the first threshold value Th1. If the first threshold value Th1 has been reached, the process proceeds to step S202, and the degree of opening control unit 216 controls the degree of opening of the urea injector in a direction to open as time passes.

If it is determined in step S201 that the NO output (NO concentration) has not reached the first threshold value Th1, the process proceeds to step S203, and the degree of opening control unit 216 determines whether or not the $NH_3$ output ($NH_3$ concentration) from the first control circuit 214A has reached the second threshold value Th2. If the second threshold value Th2 has been reached, the process proceeds to step S204, and the degree of opening control unit 216 controls the degree of opening of the urea injector in a direction to close as time passes.

At a stage at which processing by the aforementioned step S202 or step S204 is ended, or in the case it is determined in step S203 that the $NH_3$ output ($NH_3$ concentration) has not reached the second threshold value Th2, the process proceeds to the following step S205, whereupon the degree of opening control unit 216 determines whether or not the degree of opening of the urea injector has reached a predetermined degree of opening, for example, a degree of opening that is ¾ of being totally opened (referred to as a ¾ opening degree). If the degree of opening has reached the ¾ opening degree, the process proceeds to step S206, whereupon the SCR deterioration detection unit 218 calculates the NO/$NH_3$ ratio on the basis of the NO concentration and the $NH_3$ concentration from the first control circuit 214A.

At a stage at which processing by the aforementioned step S206 is ended, or in the case it is determined in step S205 that the degree of opening of the urea injector has not reached the ¾ opening degree, then in the following step S207, the SCR deterioration detection unit 218 displays information concerning the deterioration of the SCR catalyst 206 in accordance with the calculation result on the display device 222. For example, if the calculation result exceeds 1, a message is displayed indicating that the SCR catalyst 206 is deteriorated, and if the calculation result is less than or equal to 1, a message is displayed indicating that the SCR catalyst 206 is not deteriorated.

Thereafter, in step S208, in the DOC deterioration detection unit 220, the NO/$NO_2$ ratio is calculated based on the NO concentration and the $NO_2$ concentration from the second control circuit 214B. Thereafter, in step S209, the DOC deterioration detection unit 220 displays information concerning the deterioration of the DOC catalyst 204 in accordance with the calculation result on the display device 222. For example, if the calculation result exceeds 1, a message is displayed indicating that the DOC catalyst 204 is deteriorated, and if the calculation result is less than or equal to 1 (in most cases, it equals 1), a message is displayed indicating that the DOC catalyst 204 is not deteriorated.

Thereafter, in step S210, a determination is made as to whether or not there is a termination request (power off, maintenance, etc.) with respect to the exhaust gas purification system 200. If there is not a termination request, step S201 is returned to, and the processes from step S201 and thereafter are repeated. If there is a termination request, the processing carried out by the exhaust gas purification system 200 is brought to an end.

Normally, control of an SCR system and a method for carrying out failure diagnosis can be contemplated by attaching on a downstream side of the SCR catalyst a conventional two-chamber type NOx sensor and an $NH_3$ sensor in which a change in resistance of an oxide semiconductor electrode or a mixed potential is used, and by separately measuring the respective components.

However, due to differences in the sensitivity and response speeds of the respective sensors, as well as differences in the deterioration over time of the respective sensors, it has not been possible to accurately control the injected amount of urea water, or to detect deterioration of the SCR catalyst 206 over a prolonged time period.

Such a disadvantage also applies to detecting deterioration of the DOC catalyst 204, in which a method for carrying out failure detection of the DOC catalyst 204 can be contemplated by attaching on a downstream side of the DOC catalyst 204 a conventional two-chamber type NOx sensor and an $NO_2$ sensor in which a change in resistance of an oxide semiconductor electrode or a mixed potential is used, and by separately measuring the respective components.

In the exhaust gas purification system 200 according to the present embodiment, the first gas sensor 10A is used, which is capable of reliably detecting a difference in diffusion coefficients, even for an extremely unstable component such as $NH_3$, and can detect the respective concentrations of NO and $NH_3$ with a single sensor element.

More specifically, by controlling the injected amount of urea water and detecting deterioration of the SCR catalyst 206 on the basis of outputs, i.e., the NO concentration and the $NH_3$ concentration, from the single first gas sensor 10A, no adverse influence is received due to variations in output between individual sensors made up from a combination of a serial two-chamber type NOx sensor and another sensor. Furthermore, since no adverse influence is received due to variations between respective individual sensor outputs over time, purification of NOx and suppression of the $NH_3$ emission level can be carried out with high accuracy over a prolonged time period.

In addition, since deterioration of the DOC catalyst 204 is detected on the basis of outputs, i.e., the NO concentration and the $NO_2$ concentration, from the single second gas sensor 10B, it is possible to detect deterioration of the DOC catalyst 204 accurately over a prolonged time period.

The exhaust gas purification system and the exhaust gas purification method according to the present invention are not limited to the embodiments described above, and it is a matter of course that various configurations could be adopted therein without deviating from the essence and gist of the present invention.

In the example discussed above, the measurement chamber 20 is disposed adjacent to the auxiliary adjustment chamber 18b, and the measurement electrode 62 is arranged inside the measurement chamber 20. However, as shown in FIG. 20, the measurement electrode 62 may be arranged inside the auxiliary adjustment chamber 18b, and may be formed of a ceramic porous body such as alumina ($Al_2O_3$) serving as the third diffusion rate control portion 34 so as to cover the measurement electrode 62. In this case, the surrounding periphery of the measurement electrode 62 functions as the measurement chamber 20.

Further, in the above example, $NH_3$ or $NO_2$ as the second target component is converted into NO inside the preliminary adjustment chamber 21 at a conversion ratio of 100%. However, the conversion ratio of $NH_3$ or $NO_2$ need not necessarily be 100%, and the conversion ratio can be set arbitrarily, within a range in which a correlation with good reproducibility with the $NH_3$ concentration or the $NO_2$ concentration within the gas to be measured is obtained.

Further, driving of the preliminary oxygen concentration control unit 106 may be performed in a direction of pumping oxygen out from the interior of the preliminary adjustment chamber 21, or in a direction of pumping oxygen into the preliminary adjustment chamber 21, and it is sufficient insofar as the measurement pump current Ip3, which is the output of the measurement pump cell 61, changes with good reproducibility due to the presence of $NH_3$ or $NO_2$ that serves as the second target component.

Furthermore, driving of the preliminary oxygen concentration control unit 106 may turn on or off the application of a constant voltage, or may turn on or off the application of a variable voltage based on the oxygen concentration inside the preliminary adjustment chamber 21.

In addition, the driven time period and the stopped time period of the preliminary oxygen concentration control unit 106 can be arbitrarily set depending on a desired detection accuracy of the first target component and the second target component.

In practicing the present invention, various configurations for improving reliability may be added as components for an automobile to such an extent that the concept of the present invention is not impaired.

The invention claimed is:

1. A gas sensor including:
   a sensor element having a structural body made up from a solid electrolyte that exhibits oxygen ion conductivity, a gas introduction port formed in the structural body and into which a gas to be measured is introduced, an oxygen concentration adjustment chamber formed in the structural body and communicating with the gas introduction port, and a measurement chamber formed in the structural body and communicating with the oxygen concentration adjustment chamber; and
   a processor coupled to a memory storing instructions that when executed by the processor configure the processor to:
   control the oxygen concentration in the oxygen concentration adjustment chamber;
   control a temperature of the sensor element; and
   measure a concentration of a specified component in the measurement chamber;
   the gas sensor further comprising:
   a preliminary adjustment chamber provided within the structural body between the gas introduction port and the oxygen concentration adjustment chamber and a preliminary pump cell including a preliminary pump electrode that pumps oxygen in and out of the preliminary adjustment chamber, the preliminary adjustment chamber communicating with the gas introduction port, wherein the processor is further configured to:

control the oxygen concentration inside the preliminary adjustment chamber by driving the preliminary pump cell to pump oxygen in and out of the preliminary adjustment chamber;

control the driving and stopping of the preliminary pump cell; and acquire an NO concentration and an $NH_3$ concentration, on a basis of a difference between a sensor output upon the preliminary pump cell being driven, and a sensor output upon the preliminary pump cell being stopped, and one of the respective sensor outputs.

2. The gas sensor according to claim 1, wherein the sensor element comprises:

a first diffusion rate control portion between the gas introduction port and the preliminary adjustment chamber;

a second diffusion rate control portion between the preliminary adjustment chamber and the oxygen concentration adjustment chamber; and a third diffusion rate control portion between the oxygen concentration adjustment chamber and the measurement chamber.

3. The gas sensor according to claim 1, wherein:

the oxygen concentration adjustment chamber includes a main adjustment chamber communicating with the preliminary adjustment chamber, and an auxiliary adjustment chamber communicating with the main adjustment chamber; and the measurement chamber communicates with the auxiliary adjustment chamber.

4. The gas sensor according to claim 3, further comprising a fourth diffusion rate control portion between the main adjustment chamber and the auxiliary adjustment chamber.

5. The gas sensor according to claim 1, wherein:

a pump electrode is included inside the oxygen concentration adjustment chamber;

a measurement electrode is included inside the measurement chamber; and the measurement electrode is constituted by a material having a catalytic activity higher than a catalytic activity of the pump electrode.

6. The gas sensor according to claim 1, wherein the specified component is NO, a first target component is NO, and a second target component is $NH_3$.

7. The gas sensor according to claim 6, wherein the processor is further configured to, upon the preliminary pump cell being driven, control the oxygen concentration inside the preliminary adjustment chamber under a condition in which $NH_3$ is oxidized, without causing decomposition of NO inside the preliminary adjustment chamber.

8. The gas sensor according to claim 6, wherein a first map in which there is recorded a relationship, which is measured experimentally in advance, between the NO concentration and the $NH_3$ concentration respectively for each of points specified by the sensor output at a time of stopping the preliminary pump cell, and a difference in the sensor outputs at times of driving and stopping the preliminary pump cell, is stored in the memory; and wherein the processor is further configured to obtain the respective concentrations of NO and $NH_3$ by comparing with the first map the sensor outputs at the time of stopping the preliminary pump cell during actual use, and the difference in the sensor outputs at the times of driving and stopping the preliminary pump cell.

9. The gas sensor according to claim 6, wherein the processor is configured to obtain the $NH_3$ concentration corresponding to a difference in the sensor outputs at times of driving and stopping the preliminary pump cell during actual use, on a basis of a relationship, which is measured experimentally in advance, between the $NH_3$ concentration and the difference in the sensor outputs at the times of driving and stopping the preliminary pump cell; and wherein the processor is further configured to obtain the NO concentration by an operation of subtracting the $NH_3$ concentration, which was obtained beforehand from the difference in the sensor outputs, from a total NO concentration in which all of the concentrations of NO and $NH_3$ obtained from the sensor output at a time of stopping the preliminary pump cell are converted into NO.

10. The gas sensor according to claim 1, wherein the specified component is NO, a first target component is NO, and a second target component is $NO_2$.

11. The gas sensor according to claim 10, wherein the processor is further configured, upon the preliminary pump cell being driven, to control the oxygen concentration inside the preliminary adjustment chamber under a condition in which $NO_2$ is converted into NO, without causing decomposition of NO inside the preliminary adjustment chamber.

12. The gas sensor according to claim 10, wherein a second map in which there is recorded a relationship, which is measured experimentally in advance, between the NO concentration and the $NO_2$ concentration respectively for each of points specified by the sensor output at a time of stopping the preliminary pump cell, and a difference in the sensor outputs at times of driving and stopping the preliminary pump cell is stored in the memory; and wherein the processor is further configured to obtain the respective concentrations of NO and $NO_2$ by comparing with the second map the sensor output at the time of stopping the preliminary pump cell during actual use, and the difference in the sensor outputs at the times of driving and stopping the preliminary pump cell.

13. The gas sensor according to claim 10, wherein the processor is configured to obtain the $NO_2$ concentration corresponding to a difference in the sensor outputs at times of driving and stopping the preliminary pump cell during actual use, on a basis of a relationship, which is measured experimentally in advance, between the $NO_2$ concentration and the difference in the sensor outputs at the times of driving and stopping the preliminary pump cell; and wherein the processor is further configured to obtain the NO concentration by an operation of subtracting the $NO_2$ concentration, which was obtained beforehand from the difference in the sensor outputs, from a total NO concentration in which all of the concentrations of NO and $NO_2$ obtained from the sensor output at a time of stopping the preliminary pump cell are converted into NO.

14. A method of measuring concentrations of a plurality of target components in a gas to be measured, in which there is used a sensor element having a structural body made up from a solid electrolyte that exhibits at least oxygen ion conductivity, a gas introduction port formed in the structural body and into which a gas to be measured is introduced, an oxygen concentration adjustment chamber formed in the structural body and communicating with the gas introduction port, a measurement chamber formed in the structural body and communicating with the oxygen concentration adjustment chamber, a processor coupled to a memory storing instructions that when executed by the processor configure the processor to control the oxygen concentration in the oxygen concentration adjustment chamber, control a temperature of the sensor element and measure a concentration of a specified component in the measurement chamber; and a preliminary adjustment chamber provided within the structural body between the gas introduction port and the oxygen concentration adjustment chamber and a preliminary pump cell including a preliminary pump electrode that pumps oxygen in and out of the preliminary adjustment chamber, and communicating with the gas introduction port, the method comprising:

controlling the oxygen concentration inside the preliminary adjustment chamber by driving the preliminary pump cell to pump oxygen in and out of the preliminary adjustment chamber;

controlling driving and stopping of the preliminary pump cell; and a target component acquisition step of acquiring an NO concentration and an $NH_3$ concentration, on a basis of a difference between a sensor output upon the preliminary pump cell being driven, and a sensor output upon the preliminary pump cell being stopped, and one of the respective sensor outputs.

15. The method of measuring concentrations of a plurality of components in a gas to be measured according to claim 14, wherein the specified component is NO, a first target component is NO, and a second target component is $NH_3$.

16. The method of measuring concentrations of a plurality of components in a gas to be measured according to claim 15, wherein the oxygen concentration inside the preliminary adjustment chamber is controlled under a condition in which $NH_3$ is oxidized, without causing decomposition of NO inside the preliminary adjustment chamber.

17. The method of measuring concentrations of a plurality of components in a gas to be measured according to claim 15, wherein, in the target component acquisition step:

a first map is utilized in which there is recorded a relationship, which is measured experimentally in advance, between the NO concentration and the $NH_3$ concentration respectively for each of points specified by the sensor output at a time of stopping the preliminary pump cell, and a difference in the sensor outputs at times of driving and stopping the preliminary pump cell; and the respective concentrations of NO and $NH_3$ are obtained by comparing with the first map the sensor output from the specified component measurement unit at the time of stopping the preliminary pump cell during actual use, and the difference in the sensor outputs at the times of driving and stopping the preliminary pump cell.

18. The method of measuring concentrations of a plurality of components in a gas to be measured according to claim 15, wherein, in the target component acquisition step:

the $NH_3$ concentration is obtained corresponding to a difference in the sensor outputs at times of driving and stopping the preliminary pump cell during actual use, on a basis of a relationship, which is measured experimentally in advance, between the $NH_3$ concentration and the difference in the sensor outputs at the times of driving and stopping the preliminary pump cell; and the NO concentration is obtained by an operation of subtracting the $NH_3$ concentration, which was obtained beforehand from the difference in the sensor outputs, from a total NO concentration in which all of the concentrations of NO and $NH_3$ obtained from the sensor output at a time of stopping the preliminary pump cell are converted into NO.

19. The method of measuring concentrations of a plurality of components in a gas to be measured according to claim 14, wherein the specified component is NO, a first target component is NO, and a second target component is $NO_2$.

20. The method of measuring concentrations of a plurality of components in a gas to be measured according to claim 19, wherein, at a time of being driven, the preliminary pump cell controls the oxygen concentration inside the preliminary adjustment chamber under a condition in which $NO_2$ is converted into NO, without causing decomposition of NO inside the preliminary adjustment chamber.

21. The method of measuring concentrations of a plurality of components in a gas to be measured according to claim 19, wherein, in the target component acquisition step:

a second map is utilized in which there is recorded a relationship, which is measured experimentally in advance, between the NO concentration and the $NO_2$ concentration respectively for each of points specified by the sensor output at a time of stopping the preliminary oxygen pump cell, and a difference in the sensor outputs at times of driving and stopping the preliminary pump cell; and the respective concentrations of NO and $NO_2$ are obtained by comparing with the second map the sensor output at the time of stopping the preliminary pump cell during actual use, and the difference in the sensor outputs at the times of driving and stopping the preliminary pump cell.

22. The method of measuring concentrations of a plurality of components in a gas to be measured according to claim 19, wherein, in the target component acquisition step:

the $NO_2$ concentration is obtained corresponding to a difference in the sensor outputs at times of driving and stopping the preliminary pump cell during actual use, on a basis of a relationship, which is measured experimentally in advance, between the $NO_2$ concentration and the difference in the sensor outputs at the times of driving and stopping the preliminary pump cell; and the NO concentration is obtained by an operation of subtracting the $NO_2$ concentration, which was obtained beforehand from the difference in the sensor outputs, from a total NO concentration in which all of the concentrations of NO and $NO_2$ obtained from the sensor output at a time of stopping the preliminary pump cell are converted into NO.

* * * * *